US012564731B2

(12) United States Patent
Li et al.

(10) Patent No.: US 12,564,731 B2
(45) Date of Patent: Mar. 3, 2026

(54) PARTICLE TRANSPORT SIMULATION METHOD AND DEVICE

(71) Applicant: SHANGHAI UNITED IMAGING HEALTHCARE CO., LTD., Shanghai (CN)

(72) Inventors: Jiang-Feng Li, Shanghai (CN); Jia-Qi Fu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 239 days.

(21) Appl. No.: 18/231,747

(22) Filed: Aug. 8, 2023

(65) Prior Publication Data

US 2024/0050770 A1 Feb. 15, 2024

(30) Foreign Application Priority Data

Aug. 9, 2022 (CN) .......................... 202210958601.8

(51) Int. Cl.
*A61N 5/10* (2006.01)

(52) U.S. Cl.
CPC ........... *A61N 5/1031* (2013.01); *A61N 5/103* (2013.01); *A61N 2005/1034* (2013.01); *A61N 2005/1087* (2013.01)

(58) Field of Classification Search
CPC ........ A61N 5/10; A61N 5/103; A61N 5/1031; A61N 2005/1034; A61N 2005/1087; A61N 2005/1089
USPC .......................................................... 378/65
See application file for complete search history.

(56) References Cited

U.S. PATENT DOCUMENTS

| | | | | | |
|---|---|---|---|---|---|
| 5,870,697 A | * | 2/1999 | Chandler | ............. | A61N 5/1031 |
| | | | | | 378/65 |
| 6,714,620 B2 | | 3/2004 | Caflisch et al. | | |
| 7,317,192 B2 | * | 1/2008 | Ma | ......................... | H05H 15/00 |
| | | | | | 250/492.1 |
| 7,826,593 B2 | * | 11/2010 | Svensson | ............. | A61N 5/1042 |
| | | | | | 378/65 |
| 8,125,813 B2 | * | 2/2012 | Nizin | ................... | A61N 5/1031 |
| | | | | | 250/492.1 |
| 9,731,149 B2 | * | 8/2017 | Boisseau | ............. | A61N 5/1043 |
| 9,878,181 B2 | * | 1/2018 | Russo | ................. | A61N 5/1075 |
| 9,999,788 B2 | * | 6/2018 | Gattiker | ............... | A61N 5/1048 |
| 10,028,712 B2 | * | 7/2018 | Allinson | ............... | G01T 1/2985 |
| 10,376,713 B2 | * | 8/2019 | Takayanagi | .......... | A61N 5/1031 |
| 11,213,699 B2 | * | 1/2022 | Carabe-Fernandez | ...................... | |
| | | | | | G16H 20/40 |

(Continued)

FOREIGN PATENT DOCUMENTS

| | | |
|---|---|---|
| CN | 107050667 B | 5/2019 |
| CN | 113426030 A | 9/2021 |

*Primary Examiner* — Allen C. Ho

(57) ABSTRACT

The present disclosure relates to a particle transport simulation method which includes obtaining a virtual particle source, simulating a deflection of the virtual particle source under a magnetic field to obtain a deflected particle, modeling one or more of a range modulator, a beam limiting hole, and an exit window based on physical properties of the range modulator, the beam limiting hole and the exit window, respectively, to obtain one or more of a range modulator model, a beam limiting hole model, and an exit window model, and simulating physical processes of the deflected particle in the one or more of the range modulator model, the beam limiting hole model, and the exit window model, respectively.

20 Claims, 8 Drawing Sheets

300

Obtaining a virtual particle source and simulating a deflection of the virtual particle source under a magnetic field to obtain a deflected particle
310

Modeling one or more of a range modulator, a beam limiting hole, and an exit window based on physical properties of the range modulator, the beam limiting hole and the exit window, respectively, to obtain one or more of a range modulator model, a beam limiting hole model, and an exit window model
320

Simulating physical processes of the deflected particle in the one or more of the range modulator model, the beam limiting hole model, and the exit window model, respectively
330

(56)  References Cited

U.S. PATENT DOCUMENTS

| | | | |
|---|---|---|---|
| 11,235,171 B2 * | 2/2022 | Wulff .................... | A61N 5/1031 |
| 11,291,861 B2 * | 4/2022 | Cooley ................ | A61N 5/1031 |
| 11,478,665 B2 * | 10/2022 | Snider, III ........... | A61N 5/1042 |
| 11,701,526 B2 * | 7/2023 | Carabe-Fernandez ....................... | |
| | | | A61N 5/1031 |
| | | | 600/1 |
| 12,239,853 B2 * | 3/2025 | Shi ....................... | A61N 5/1075 |

* cited by examiner

200

Virtual particle source obtaining module

210

Modeling module

220

Simulation module

Figure 3:
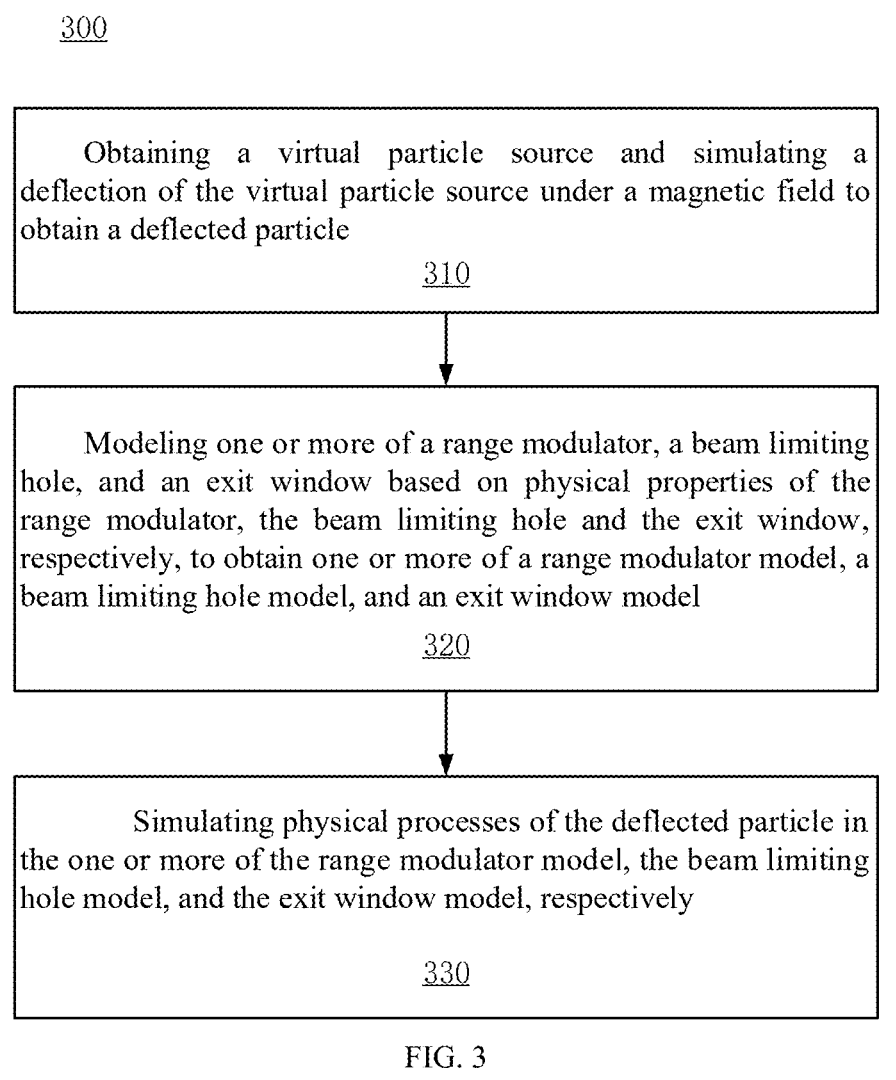

Obtaining a virtual particle source and simulating a deflection of the virtual particle source under a magnetic field to obtain a deflected particle

310

Modeling one or more of a range modulator, a beam limiting hole, and an exit window based on physical properties of the range modulator, the beam limiting hole and the exit window, respectively, to obtain one or more of a range modulator model, a beam limiting hole model, and an exit window model

320

Simulating physical processes of the deflected particle in the one or more of the range modulator model, the beam limiting hole model, and the exit window model, respectively

P<sub>a</sub>·A'
    P<sub>d</sub>
6a    A"
        A'''

P<sub>b</sub>
6b

P<sub>c</sub>·  G
6c    F·

P<sub>d</sub>·  J
6d    I·

M ......                                    ...... M'

603

604

605

606

PARTICLE TRANSPORT SIMULATION METHOD AND DEVICE

CROSS-REFERENCE TO RELATED APPLICATIONS

The present application claims the priority to Chinese Patent Application with No. 202210958601.8, entitled "Particle Transport Simulation Method, System and Device" and filed on Aug. 9, 2022, the content of which is incorporated herein by reference in its entirety.

TECHNICAL FIELD

The present disclosure relates to the field of radioactive therapy technology, and particularly to a method for simulating particle transport, a particle transport simulation device, and a non-transitory storage medium.

BACKGROUND

The radiotherapy system refers to a device using a particle beam to kill a tumor. According to an active scanning method (also referred to as pencil beam scanning method), a treatment head can be used to adjust the direction and range of the particle beam to adapt the particle beam to the position and depth of the tumor. In order to calculate the radiotherapy dose of the particle beam, it is necessary to model the particle beam and the physical process of the particle beam in the treatment head.

However, the particle beam has a wide energy range and many energy levels, and the modeling efficiency of the particle source is low and the accuracy is limited. In addition, the modeling of the treatment head and the mold body for receiving the dose is complex, and the modeling efficiency is difficult to satisfy the clinical requirements.

SUMMARY

One aspect of the present disclosure provides a method for simulating particle transport. The method includes obtaining a virtual particle source, simulating a deflection of the virtual particle source under a magnetic field to obtain a deflected particle, modeling one or more of a range modulator, a beam limiting hole, and an exit window based on physical properties of the range modulator, the beam limiting hole and the exit window, respectively, to obtain one or more of a range modulator model, a beam limiting hole model, and an exit window model, and simulating physical processes of the deflected particle in the one or more of the range modulator model, the beam limiting hole model, and the exit window model, respectively.

Another aspect of the present disclosure provides a particle transport simulation device. The device includes at least one processor and at least one memory storing computer instructions therein. The at least one processor, when executing at least a part of the computer instructions, performs a method for simulating particle transport. The method includes obtaining a virtual particle source, simulating a deflection of the virtual particle source under a magnetic field to obtain a deflected particle, modeling one or more of a range modulator, a beam limiting hole, and an exit window based on physical properties of the range modulator, the beam limiting hole and the exit window, respectively, to obtain one or more of a range modulator model, a beam limiting hole model, and an exit window model, and simulating physical processes of the deflected particle in the one or more of the range modulator model, the beam limiting hole model, and the exit window model, respectively.

Yet another aspect of the present disclosure provides a non-transitory computer-readable storage medium storing instructions that, when executed by one or more processors, cause the one or more processors to perform a method for simulating particle transport. The method includes obtaining a virtual particle source, simulating a deflection of the virtual particle source under a magnetic field to obtain a deflected particle, modeling one or more of a range modulator, a beam limiting hole, and an exit window based on physical properties of the range modulator, the beam limiting hole and the exit window, respectively, to obtain one or more of a range modulator model, a beam limiting hole model, and an exit window model, and simulating physical processes of the deflected particle in the one or more of the range modulator model, the beam limiting hole model, and the exit window model, respectively.

BRIEF DESCRIPTION OF THE DRAWINGS

Exemplary embodiments will be further described in this specification, and these exemplary embodiments will be described in detail with the accompanying drawings. These embodiments are not limiting, and in these embodiments, the same reference numerals indicate the same structure.

FIG. 2 is an exemplary block diagram of a particle transport simulation system according to some embodiments of the present disclosure;

FIG. 3 is an exemplary flow chart of a particle transport simulation method according to some embodiments of the present disclosure;

DETAILED DESCRIPTION

In order to illustrate more clearly the technical solution of the embodiments of the present disclosure, the accompanying drawings to be used in the description of the embodiments are briefly described below. It will be obvious that the accompanying drawings described below are merely examples or embodiments of the present disclosure, which may also be applied to other similar situations in accordance with these drawings by one of ordinary skill in the art without incurring creative labor. Unless otherwise apparent from the locale or otherwise indicated, the same reference signs in the figures represent the same structure or operation.

It should be appreciated that "system", "device", "unit" and/or "module" as used herein are intended to distinguish different levels of assemblies, elements, components, portions, or assembling. However, if other words and expressions may achieve the same purpose, the above words may be replaced by other words and expressions.

As shown in the present specification and claims, unless the context expressly indicates an exception, the words "a", "one", "an" and/or "the" do not specifically mean singular but may include multiple. In general, the terms "comprising" and "including" imply only explicitly identified steps and elements that do not constitute an exclusive enumeration, and the method or apparatus may further include other steps or elements.

Flow charts are used in this specification to illustrate operations performed by a system according to embodiments of the present disclosure. It should be appreciated that the previous or subsequent operations are not necessarily performed precisely in order. Instead, the steps can be processed in reverse order or concurrently. Meanwhile, other operations can also be added into these procedures or one or more steps are removed from these procedures.

Figure 1:
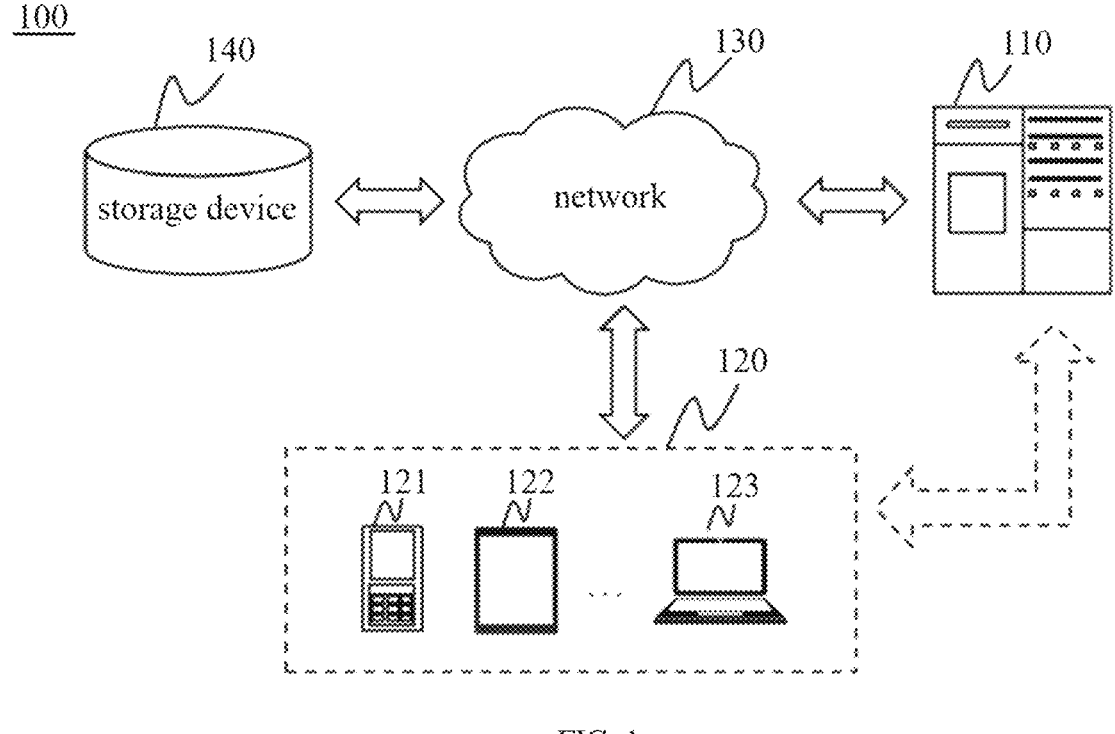
FIG. 1 is a schematic diagram of an application scenario for a particle transport simulation system according to some embodiments of the present disclosure.

FIG. 1 is a schematic diagram of an application scenario for a particle transport simulation system according to some embodiments of the present disclosure.

The particle transport simulation system is applied in a modeling system. A treatment head of a radioactive therapy system may be modeled by implementing the method and/or process disclosed herein. As shown in FIG. 1, a modeling system 100 may include a processing device 110, a terminal device 120, a network 130, and/or a storage device 140, etc.

Components of the modeling system 100 may be connected in one or more different manners. As an example, only, as shown in FIG. 1, the processing device 110 may be connected to the storage device 140 through the network 130. As another example, the processing device 110 may be directly connected to the terminal device 120 (as indicated by the dashed bidirectional arrows connecting the processing device 110 and the terminal device 120). As a further example, the storage device 140 may be connected to the processing device 110 either directly or through the network 130. As a further example, the terminal device 120 may be connected to the processing device 110 directly (as shown by the dashed bidirectional arrows connecting the terminal device 120 and the processing device 110) and/or through the network 130.

The processing device 110 may process data and/or information obtained from the terminal device 120 and/or the storage device 140. For example, the processing device 110 may obtain a treatment plan from the storage device 140. For another example, the processing device 110 may model a treatment head based on a treatment plan. In some embodiments, the processing device 110 may include a central processing unit (CPU), a digital signal processor (DSP), a system on chip (SOC), a microcontroller unit (MCU), etc., and/or any combination thereof. In some embodiments, the processing device 110 may include a computer, a user console, a single server, or a group of servers, etc. A group of servers may be centralized or distributed. In some embodiments, the processing device 110 may be local or remote. For example, the processing device 110 may access information and/or data stored in the terminal device 120 and/or storage device 140 through the network 130. For another example, the processing device 110 may be directly connected to the terminal device 120 and/or the storage device 140 to access the stored information and/or data. In some embodiments, the processing device 110 may be implemented on a cloud platform. As an example, only, the cloud platform may include a private cloud, a public cloud, a hybrid cloud, a community cloud, a distributed cloud, intercloud, multi-cloud, etc., or any combination thereof.

The terminal device 120 may display a model to a user (e.g., a range modulator model, a beam limiting model, and an exit window model). The terminal device 120 may include a mobile device 121, a tablet computer 122, a notebook computer 123, etc., or any combination thereof. In some embodiments, the terminal device 120 may be a part of the processing device 110.

The network 130 may include any appropriate network that facilitates the exchange of information and/or data for the modeling system 100. In some embodiments, one or more components of the modeling system 100 (e.g., the processing device 110, the storage device 140, or the terminal device 120) may communicate information and/or data with one or more other components of the modeling system 100 through the network 130. For example, the processing device 110 may obtain a treatment plan from the storage device 140 through the network 130. For another example, the terminal device 120 may obtain a model parameter from the processing device 110 through the network 130. The network 130 may be and/or include a public network, a private network, a wide area network (WAN), a wired network, a wireless network, a cellular network, a frame relay network, a virtual private network, a satellite network, a telephone network, a router, a hub, a switch, a server computer, and/or any combination thereof. In some embodiments, the network 130 may include one or more network access points. For example, the network 130 may include wired and/or wireless network access points, such as base stations and/or internet switching points, through which one or more components of the modeling system 100 may connect to the network 130 to exchange data and/or information.

The storage device 140 may store data, instructions, and/or any other information. In some embodiments, the storage device 140 may store data obtained from the terminal device 120 and/or the processing device 110. For example, the storage device 140 may store an initial energy distribution, an initial position distribution, and an initial angle distribution of a virtual particle source. For another example, the storage device 140 may store a state of a simulated secondary particle. In some embodiments, the storage device 140 may include a mass memory, a removable memory, transitory read and write memory, a read only memory (ROM), or any combination thereof. In some embodiments, the storage device 140 may be implemented on a cloud platform. In some embodiments, the storage device 140 may be connected to the network 130 to communicate with one or more other components of the modeling system 100 (e.g., the processing device 110, or the terminal device 120). One or more components of the modeling system 100 may access data or instructions stored in the storage device 140 through the network 130. In some embodiments, the storage device 140 may be directly connected to or in communication with one or more other components of the modeling system 100 (e.g., the processing device 110, the storage device 140, or the terminal device 120). In some embodiments, the storage device 140 may be a part of the processing device 110.

Figure 2:
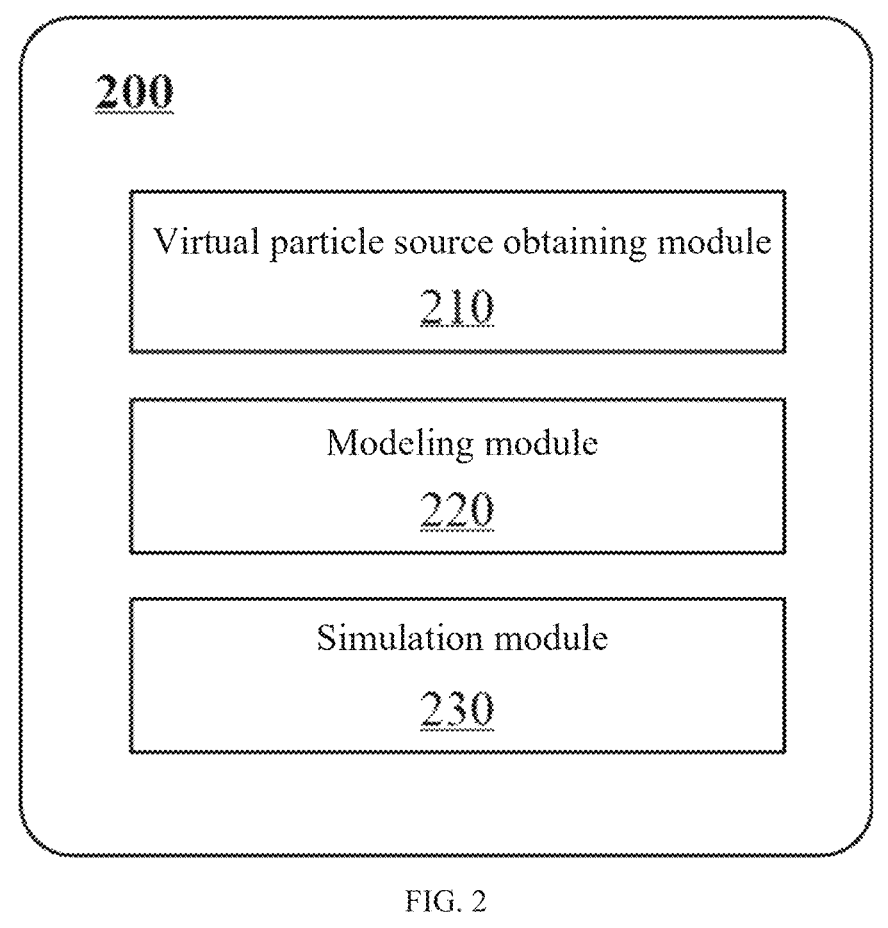

FIG. 2 is an exemplary block diagram of a particle transport simulation system according to some embodiments of the present disclosure. As shown in FIG. 2, the particle transport simulation system 200 may include a virtual particle source obtaining module 210, a modeling module 220, and a simulation module 230.

The virtual particle source obtaining module 210 is configured to obtain a virtual particle source, simulate a deflection of the virtual particle source under a magnetic field, and obtain a deflected particle. In some embodiments, the virtual particle source obtaining module 210 may obtain an initial energy value, an initial position, and an initial angle of the virtual particle source based on a probability distribution function.

The modeling module 220 may be configured to model the range modulator, the beam limiting hole, and the exit window based on physical properties of the range modulator, the beam limiting hole, and the exit window, to obtain the range modulator model, the beam limiting hole model, and the exit window model. In some embodiments, the modeling module 220 may divide the range modulator, the beam limiting hole, and the exit window into at least one grid respectively based on the physical properties of the range modulator, the beam limiting hole, and the exit window, to obtain the range modulator model, the beam limiting hole model, and the exit window model. In some embodiments, the modeling module 220 may divide each layer of the range modulator into a first gird in a thickness direction of the range modulator based on the structure, dimension of the range modulator, and/or a property of an absorption material of the range modulator. In some embodiments, the modeling module 220 may divide the exit window into a second grid. In some embodiments, the modeling module 220 may perform one or more of the following steps: determining a flux value corresponding to each of a plurality of third grids based on a shape of the cross-section of the beam limiting hole, or determining a density value corresponding to each of the plurality of third grids based on the flux value corresponding to each third grid and a material density of the beam limiting hole. In some embodiments, the flux value may represent an occlusion rate of the third grid against the deflected particle.

The simulation module 230 may be configured to simulate physical processes of the deflected particle in the range modulator model, the beam limiting hole model, and the exit window model. In some embodiments, the simulation module 230 may be configured to simulate a collision path and an energy loss of the deflected particle in the beam limiting hole model based on the density value corresponding to each third grid. In some embodiments, the simulation module 230 may be configured to perform one and/or more of the following steps: simulating a secondary particle generated by the deflected particle in the range modulator model, determining whether the secondary particle is able to pass through the range modulator model, storing a state of the secondary particle in response to the passage of the secondary particle through the range modulator model.

FIG. 3 is an exemplary flow chart of a particle transport simulation method according to some embodiments of the present disclosure.

A radioactive therapy system may be a device that uses a particle beam to kill a tumor. In some embodiments, a radioactive therapy system may include, but is not limited to, an X-ray therapy machine, a γ-ray after loader, a gamma knife, a neutron after loader, a neutron knife, a cyberknife, a Tomotherapy, an isotope teletherapy machine and/or a proton therapy system (PTS), etc.

In some embodiments, the radioactive therapy system may include a beam generation system (i.e., an accelerator system), an energy selection system, a beam transport system, and a beam irradiation system. Specifically, the beam generation system can generate a particle beam. The energy selection system can adjust the energy of the particle beam so that the particle beam can reach different depths of the tumor. The beam transport system can transport the particle beam to the beam irradiation system. The beam irradiation system can accurately irradiate a required dose to the tumor by controlling the transport of the beam.

In some embodiments, the radioactive therapy system may include a treatment head.

The treatment head may be a beam control device that enables the particle beam to conform to a requirement of a radiotherapy plan. In some embodiments, the treatment head may convert a property of the particle beam (e.g., energy, direction, or position distribution) into a dose parameter (e.g., an irradiation field position, an irradiation field size, or a dose distribution, etc.) required for a radiotherapy plan. In some embodiments, the particle beam may include a proton beam, a heavy ion beam, etc.

Figure 4:
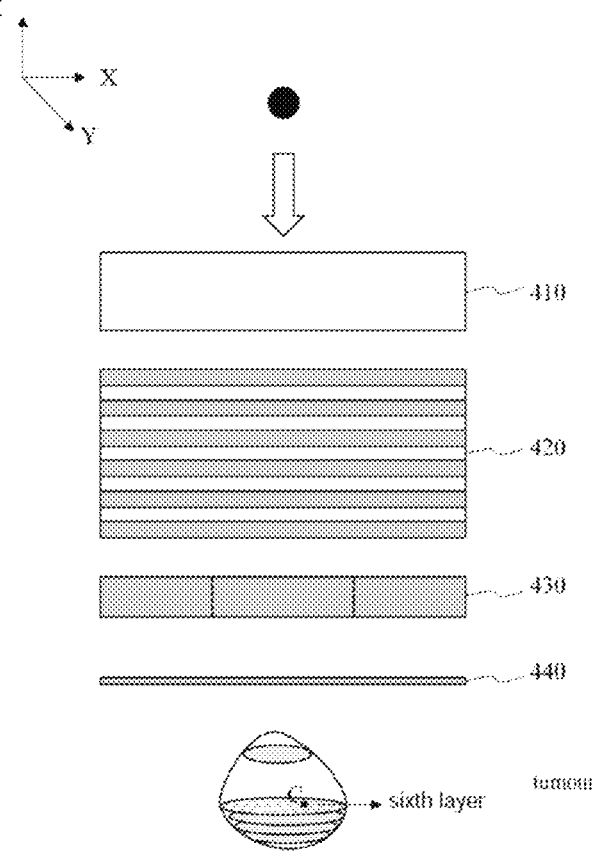
FIG. 4 is an exemplary schematic diagram of an active scanning method according to some embodiments of the present disclosure.

In some embodiments, the conversion mode of the particle beam may include an active scanning method (also referred to as pencil beam scanning method)). FIG. 4 is an exemplary schematic diagram of an active scanning method according to some embodiments of the present disclosure. As shown in FIG. 4, the active scanning method can divide the tumor into a plurality of layers according to positions and widths of Bragg peaks corresponding to particle beams with different energy levels, and each layer can be divided into a plurality of scanning points according to a beam spot size of a particle beam, and the treatment head can scan the tumor layer by layer, and spot by spot.

In some embodiments, the particle transport simulation system 200 may model the treatment head to calculate the particle radiotherapy dose to the tumor by the beam irradiation system based on the model.

As shown in FIG. 3, a method 300 for simulating particle transport includes the following steps 310-330.

In the step 310, a virtual particle source is obtained, a deflection of the virtual particle source under a magnetic field is simulated to obtain a deflected particle. Specifically, the step 310 may be performed by the virtual particle source obtaining module 210.

A particle source generation device is provided, which may be a device configured to provide a particle beam. In some embodiments, the particle source generation device may be a particle accelerator in a beam generation system. Specifically, the particle accelerator may accelerate charged particles to the required energy in the electric field and generate a certain particle beam. Further, the radioactive therapy system may utilize the beam transport system to transport the particle beam to the beam irradiation system.

A virtual particle source may be an equivalent source model of a particle beam output by the beam transport system. In some embodiments, the virtual particle source may simulate a state of each particle in a particle beam generated by the particle accelerator after the particle beam passes through the beam transport system. In some embodiments, the virtual particle source may simulate an alternate description of the state of each particle in the particle beam at a cross-section of an exit of the beam transport system (i.e., a sampling cross-section).

Figure 5:
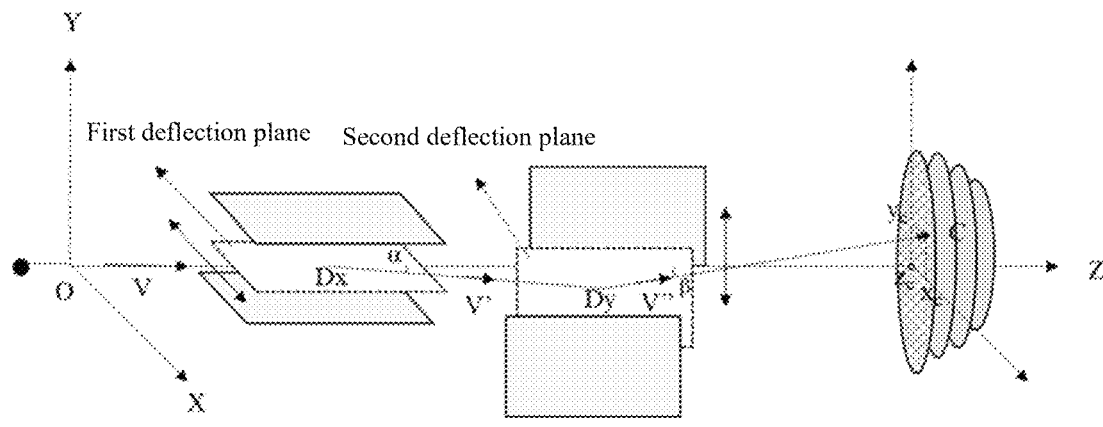
FIG. 5 is an exemplary schematic diagram showing particle deflection angles of particles being caused by scanning magnets according to some embodiments of the present disclosure.

As shown in FIGS. 4-5, for ease of calculation and description, a direction perpendicular to the tumor layer may be set to a Z-axis direction, a horizontal direction of the tumor layer may be set to an X-axis direction, a vertical direction of the tumor layer may be set to a Y-axis direction, and a center point O of, for example, the radioactive therapy device, may be set as an origin. Accordingly, an OXYZ coordinate system is established.

In some embodiments, the virtual particle source obtaining module 210 may obtain an initial energy distribution, an initial position distribution, and an initial angle distribution of the virtual particle source.

In some embodiments, the virtual particle source obtaining module 210 may obtain an initial energy value, an initial position, and an initial angle of the virtual particle source based on a probability distribution function.

The initial energy value of a particle may be an energy value of the particle in the particle beam at the sampling cross-section.

The initial energy distribution of the virtual particle source may be a statistic of the initial energy values of the particles in the particle beam.

In some embodiments, the virtual particle source obtaining module 210 may obtain the initial energy distribution of the virtual particle source based on a single Gaussian distribution.

The single Gaussian distribution may be a probability distribution with one random variable. In some embodiments, the virtual particle source obtaining module 210 may determine a single Gaussian distribution of the particle initial energy based on an average value and a standard deviation of the initial energy values of the particles in the particle beam.

The average value of the initial energy values of the particles describes a symmetrical axis position of the single Gaussian distribution of the particle initial energy, and is configured to indicate a concentration trend of the initial energy values of the particles. As an example, the higher the average value of the particle initial energy values, the greater the initial energy corresponding to the symmetrical axis position of the single Gaussian distribution of the particle initial energy, which indicates that the particle initial energy values of the particle beam have relatively larger values.

The standard deviation of the particle initial energy can describe a dispersion degree of the single Gaussian distribution of the particle initial energy, and is configured to indicate the distribution trend of the initial energy values of the particles. As an example, the larger the standard deviation of the particle initial energy, the flatter the single Gaussian distribution curve of the particle initial energy, which indicates that the distribution of the initial energy values of the particles in the particle beam is more dispersed.

In some embodiments, the virtual particle source obtaining module 210 may determine the average value and the standard deviation of the particle initial energy according to the radiotherapy plan. Specifically, the virtual particle source obtaining module 210 may calculate the average value and the standard deviation of the particle initial energy values of the particle beam corresponding to a current scanning point based on an average value and a standard deviation of a planned dose distribution corresponding to each scanning point on each tumor layer in the radiotherapy plan.

In some embodiments, the single Gaussian distribution of the particle initial energy is obtained according to the following formula (1):

$$E \sim N(E_0, \sigma_E) \tag{1}$$

where E is the single Gaussian distribution of the particle initial energy, $E_0$ is the average value of the particle initial energy values, and $\sigma_E$ is the standard deviation of the particle initial energy values of the particles.

For example, as shown in FIG. 4, the tumor layer is parallel to an isocentric plane. The average value of the particle initial energy values of the particle beam corresponding to a scanning point C on the sixth tumor layer is 90 MeV, and the standard deviation is 5 MeV, so the single Gaussian distribution of the particle initial energy is N (90, 5).

Further, in some embodiments, the virtual particle source obtaining module 210 may generate a first random number, and then obtain a particle initial energy corresponding to the first random number from the single Gaussian distribution of the particle initial energy. For example, when the particle initial energy corresponding to the first random number is 100 MeV, then the initial energy value of the particle A in the virtual particle source is 100 MeV.

The particle initial position may be a position of a particle in the particle beam on the sampling cross-section. In some embodiments, the particle initial position may include a position in the X-axis direction and a position in the Y-axis direction on the sampling cross-section.

The initial position distribution of the virtual particle source may be a statistic of the initial positions of the particles in the particle beam.

In some embodiments, the virtual particle source obtaining module 210 may obtain the initial position distribution of the virtual particle source based on a double Gaussian distribution without covariance and a double Gaussian distribution with covariance.

The double Gaussian distribution without covariance may be a probability distribution with two irrelevant random variables. In some embodiments, both Gaussian distributions in the double Gaussian distribution without covariance may correspond to initial position distributions of the virtual particle source on the X-axis and the Y-axis, respectively.

In some embodiments, the virtual particle source obtaining module 210 may obtain the double Gaussian distribution without covariance of the particle initial positions based on the average value of the particle initial positions and the standard deviation of the particle initial positions.

The average value of the particle initial positions can represent the position of a symmetric axis of the double Gaussian distribution without covariance of the particle initial positions, and is configured to indicate a concentration trend of the particle initial positions. From the description above, the coordinate of the center position of the virtual particle source on the X-axis and the Y-axis is 0. Accordingly, in some embodiments, the average value of the particle initial positions of the particle beam on the X-axis and Y-axis provided by the virtual particle source may be 0.

The standard deviation of the particle initial positions can represent the dispersion degree of the double Gaussian distribution without covariance of the particle initial positions, and is configured to indicate the distribution trend of the particle initial positions. As an example, the larger the standard deviation of the particle initial positions on the X-axis, the flatter the Gaussian distribution curve corresponding to the X-axis, indicating that the more dispersed the value distribution of the initial positions of the particles in the particle beam on the X-axis, and the larger the beam spot size corresponding to the particle beam in the X-axis direction. The larger the standard deviation of the particle initial positions on the Y-axis, the flatter the Gaussian distribution curve corresponding to the Y-axis, indicating that the more dispersed the value distribution of the initial positions of the particles in the particle beam on the Y-axis, and the larger the beam spot size corresponding to the particle beam in the Y-axis direction.

In some embodiments, the virtual particle source obtaining module 210 may determine the standard deviation of the particle initial positions based on the radiotherapy plan. Specifically, the virtual particle source obtaining module 210 may calculate the standard deviation of the particle initial positions of the particles in the particle beam corresponding to a current scanning point based on an irradiation field size corresponding to each scanning point on each tumor layer in the radiotherapy plan.

In some embodiments, the virtual particle source obtaining module 210 may be configured to obtain a double Gaussian distribution without covariance of the particle initial positions $x_2$ and $y_2$ according to the following formula (2):

$$\begin{cases} x_1 \sim N(0, \sigma_x) \\ y_1 \sim N(0, \sigma_y) \end{cases} \tag{2}$$

where $\sigma_x$ and $\sigma_y$ denote the standard deviations of the positions of the particles on the X-axis and the Y-axis, respectively.

Continuing with the above example, as shown in FIG. 4, the standard deviation of the initial positions of the particles in the particle beam corresponding to the scanning point C on the sixth tumor layer satisfies $\sigma_x$=5 cm and $\sigma_y$=6 cm, and the double Gaussian distribution without covariance of the particle initial positions includes the distribution N (0, 5) of the particle initial positions on the X-axis and the distribution N (0, 6) of the particle initial positions on the Y-axis.

Further, in some embodiments, the virtual particle source obtaining module 210 may generate a second random number, and then obtain a first initial position of a particle corresponding to the second random number from the double Gaussian distribution without covariance of the particle initial positions. For example, when the first initial position corresponding to the second random number is (6 cm, 4 cm), the first initial position of the particle A in the virtual particle source is (6 cm, 4 cm).

The double Gaussian distribution with covariance may be a probability distribution with two correlated random variables. In some embodiments, both Gaussian distributions in the double Gaussian distribution with covariance may correspond to initial location distributions of the virtual particle source on the X-axis and the Y-axis, respectively.

In some embodiments, the virtual particle source obtaining module 210 may obtain the double Gaussian distribution with covariance of the particle initial positions based on the standard deviation and covariance of the particle initial positions.

The covariance of the particle initial positions of the particles can represent a correlation between an initial position of a particle in the particle beam on the X-axis and an initial position of the particle in the particle beam on the Y-axis.

As an example, when the covariance of the particle initial positions is equal to zero, the particle initial position on the X-axis is independent of the particle initial position on the Y-axis. For example, the shape of the beam spot of the particle beam may be a circle or an ellipse that is symmetrical about the X-axis and Y-axis, and a radius of the circle or ellipse may coincide with the X-axis or Y-axis.

As another example, when the covariance of the particle initial positions is a positive value, the particle initial position on the X-axis is positively correlated with the particle initial position on the Y-axis, and the greater the absolute value of the covariance, the greater the correlation. For example, the shape of the beam spot of the particle beam may be an ellipse, and a radius along the long axis of the ellipse has a positive slope.

As another example, when the covariance of the particle initial positions is a negative value, the particle initial position on the X-axis is negatively correlated with the particle initial position on the Y-axis, and the greater the absolute value of the covariance, the greater the correlation. For example, the shape of the beam spot of the particle beam may be an ellipse, and a radius along the long axis of the ellipse has a negative slope.

In some embodiments, the virtual particle source obtaining module 210 may determine the covariance of the particle initial positions based on the radiotherapy plan. Specifically, the virtual particle source obtaining module 210 may calculate the covariance of the particle initial positions of the particles in the particle beam corresponding to a current scanning point based on a shape of a radiation field corresponding to each scanning point on each tumor layer in the radiotherapy plan.

In some embodiments, the virtual particle source obtaining module 210 may obtain the double Gaussian distribution with covariance of the particle initial positions $x_2$ and $y_2$ according to the following formula (3):

$$\begin{cases} x_2 \sim N\left(0, \sqrt{\sigma_x^2 - \sigma_{xy}^2/\sigma_y^2}\right) \\ y_2 \sim N\left(0, \sqrt{\sigma_y^2 - \sigma_{yx}^2/\sigma_x^2}\right) \end{cases} \tag{3}$$

where $\sigma_x$ and $\sigma_y$ are the standard deviations of the particle initial positions of the particles in the particle beam on the X-axis and the Y-axis, respectively, $\sigma_{xy}$ is a covariance of the particle initial positions of the particles in the particle beam on the X-axis, and $\sigma_{yx}$ is a covariance of the particle initial positions of the particles in the particle beam on the Y-axis.

Continuing with the above example, as shown in FIG. 4, the standard deviation of the particle initial positions of the particles in the particle beam corresponding to the scanning point C on the sixth tumor layer satisfies $\sigma_x$=5 cm, $\sigma_y$=6 cm, and the covariance satisfies $\sigma_{xy}$=0.8, and $\sigma_{yx}$=0.8. Accordingly, the double Gaussian distribution with covariance of the particle initial positions may include a distribution of the particle initial positions on the X-axis N(0, 5), and a distribution of the particle initial positions on the Y-axis N(0, 6).

Further, in some embodiments, the virtual particle source obtaining module 210 may obtain a second initial position of a particle corresponding to a third random number from the double Gaussian distribution with covariance of the particle initial positions. For example, the second initial position corresponding to the third random number is (5 cm, 4 cm), and then the second initial position of the particle A in the virtual particle source is (5 cm, 4 cm).

Further, in some embodiments, the virtual particle source obtaining module 210 may obtain the particle initial positions according to the following formula (4):

$$\begin{cases} x = x_2 + x_1 \cdot \sigma_{xy}/\sigma_x^2 \\ y = y_2 + y_1 \cdot \sigma_{yx}/\sigma_y^2 \end{cases} \tag{4}$$

where $x_2$ and $x_1$ are the second initial positions of the particle on the X-axis, respectively, $\sigma_{xy}$ is the covariance of the initial positions of the particles on the X-axis, $\sigma_x$ is the standard deviation of the initial positions of the particles on the X-axis, $y_2$ and $y_1$ are the second initial positions of the particle on the Y-axis, respectively, $\sigma_{yx}$ is the covariance of the initial positions of the particles on the Y-axis, and $\sigma_y$ is the standard deviation of the initial positions of the particles on the Y-axis.

Continuing with the example above, the initial position of the particle A in the virtual particle source is (5.12 cm, 4.09 cm).

In some embodiments of the present disclosure, the initial position distribution of the virtual particle source is obtained based on the double Gaussian distribution with covariance, which can not only adjust the dimension of the beam spot of the particle beam, but also adjust the slopes of the long axis and the short axis of the beam spot, so that the virtual particle source can be adapted to the shapes of the beam spots of various particle beams, thereby increasing the degrees of freedom of the adjustment of the virtual particle source.

The initial angle of a particle may be an angle of a motion direction of the particle in the particle beam on a sampling cross-section. In some embodiments, the particle initial angle may include an angle of the motion direction on the sampling cross-section deviated from the X-axis, and an angle of the motion direction on the sampling cross-section deviated from the Y-axis.

An initial angle distribution of the virtual particle source may be a statistic of the particle initial angles of the particles in the particle beam.

In some embodiments, the virtual particle source obtaining module 210 may obtain an initial angle distribution of the virtual particle source based on the double Gaussian distribution without covariance.

In some embodiments, the virtual particle source obtaining module 210 may obtain the double Gaussian distribution without covariance of the particle initial angles based on an average value and a standard deviation of the particle initial angles.

The average value of the particle initial angles can describe an angle corresponding to a symmetric axis of the double Gaussian distribution without covariance of the particle initial angles, and is configured to represent a concentration trend of the particle initial angles. From the description above, the coordinates of the center position of the virtual particle source on both the X and Y axes are 0, i.e., the Z-axis is able to pass through the center position of the virtual particle source. Accordingly, in some embodiments, the average value of the initial angles of the particle beam provided by the virtual particle source deviated from the X-axis may be equal to 0, and the average value of the initial angles of the particle beam provided by the virtual particle source deviated from the Y-axis may be equal to 0.

The standard deviation of the particle initial angles may describe a dispersion degree of the double Gaussian distribution without covariance of the particle initial angles, and is configured to represent a distribution trend of the particle initial angles. As an example, the greater the standard deviation of the particle initial angles deviated from the X-axis, the flatter the corresponding Gaussian distribution curve, which indicates that the initial angles of the motion directions of the particles in the particle beam deviated from the X-axis are more dispersed. The greater the standard deviation of the particle initial angles deviated from the Y-axis, the flatter the corresponding Gaussian distribution curve, which indicates that the initial angles of the motion directions of the particles in the particle beam deviated from the Y-axis are more dispersed.

In some embodiments, the virtual particle source obtaining module 210 may determine the standard deviation of the particle initial angles based on the radiotherapy plan. Specifically, the virtual particle source obtaining module 210 may obtain measurement data of the particle beam in the treatment head of the radiotherapy device (e.g., a profile curve of the beam spot of the particle beam) and then obtain the standard deviation of the initial angles of the particles in the particle beam corresponding to a current scanning point based on the measurement data. In some embodiments, the measurement data of different radiotherapy devices may be different.

In some embodiments, the virtual particle source obtaining module 210 may obtain the double Gaussian distribution without covariance of the particle initial angles $\theta_x$ and $\theta_y$, according to the following formula (5):

$$\begin{cases} \theta_x \sim N(0, \sigma_\gamma) \\ \theta_y \sim N(0, \sigma_\delta) \end{cases} \tag{5}$$

where $\sigma_\gamma$ and $\sigma_\delta$ are angle standard deviations of the particles deviated from the X-axis and the Y-axis, respectively.

Continuing with the above example, as shown in FIG. 4, the standard deviation of the initial angles of the particle beam corresponding to the scanning point C on the sixth tumor layer satisfies $\sigma_\gamma = 60°$, and $\sigma_\delta = 60°$. Accordingly, the double Gaussian distribution without covariance of the particle initial angles includes a distribution of the initial angles deviated from the X-axis $N(0, 60°)$, and a distribution of the initial positions deviated from the Y-axis $N(0, 60°)$.

Further, in some embodiments, the virtual particle source obtaining module 210 may generate a fourth random number, and then obtain an initial angle of a particle corresponding to the fourth random number from the double Gaussian distribution without covariance of the particle initial angles.

As an example, the particle initial angle of the particle A in the virtual particle source is (70°, 60°).

It can be seen that the initial energy value of the particle A is 100 MeV, the initial position is (5.12 cm, 4.09 cm), and the initial angle is (70°, 60°). Similarly, the first random number, the second random number, . . . , and the fourth random number can be picked multiple times, and particle initial energy values, particle initial positions and particle initial angles of the particle B, particle C, etc. in the virtual particle source are determined. Accordingly, the virtual particle source is obtained.

In some embodiments, the treatment head may include a scanning magnet, a range modulator, a beam limiting hole, and an exit window. For example, as shown in FIG. 4, the particle beam may pass through the scanning magnet 410, the range modulator 420, the beam limiting hole 430, and the exit window 440 in the treatment head sequentially.

The scanning magnet 410 may be a device configured to control the direction of the particle beam. In some embodiments, the scanning magnet may be configured to control the particle beam to deflect to a planned position, thereby adjusting the irradiation direction of the particle beam.

The planned position may be an irradiation position of the particle beam specified in the particle treatment plan. In some embodiments, the planned position may be any scanning point for an active scanning method (also referred to as pencil beam scanning method). FIG. 5 shows an exemplary scanning magnet according to some embodiments of the present disclosure. As shown in FIG. 5, for example, the planned position may be the scanning point C on the sixth tumor layer.

In some embodiments, the scanning magnet may include a first scanning magnet and a second scanning magnet.

The first scanning magnet may be a magnet that controls the particle beam to deflect in the X-axis direction. In some embodiments, the first scanning magnet may include two magnets parallel to the XZ plane. In some embodiments, the first scanning magnet may generate a first magnetic field between two magnets parallel to the XZ plane.

A first deflection angle may be an angle that the particle beam is deflected in the X-axis direction after passing through the first magnetic field. As shown in FIG. 5, the first deflection angle is denoted as $\alpha$.

A first deflection plane may be a plane in which the first deflection angle is located. In some embodiments, the first deflection plane may be parallel to the XZ plane. As shown in FIG. 5, the plane in which the first deflection angle $\alpha$ is located is the first deflection plane.

A first deflection position may be a position at which the particle begins to deflect on the first deflection plane. In some embodiments, the first deflection position may be a central position on the first deflection plane. As shown in FIG. 5, the first deflection position is a central position $D_x$ on the first deflection plane.

The second scanning magnet may be a magnet that controls the particle beam to deflect in the Y-axis direction. In some embodiments, the second scanning magnet may include two magnets parallel to the YZ plane. In some embodiments, the second scanning magnet may generate a second magnetic field between the two magnets parallel to the YZ plane.

A second deflection angle may be an angle that the particle beam is deflected in the Y-axis direction after passing through the second magnetic field. As shown in FIG. 5, the second deflection angle may be $\beta$.

A second deflection plane may be a plane in which the second deflection angle is located. In some embodiments, the second deflection plane may be parallel to the YZ plane. As shown in FIG. 5, the plane in which the second deflection angle $\beta$ is located is the second deflection plane.

The second deflection position may be a position at which the particle begins to deflect on the second deflection plane. In some embodiments, the second deflection position may be a central position on the second deflection plane. As shown in FIG. 5, the second deflection position is a central position $D_y$ on the second deflection plane.

In some embodiments, the virtual particle source obtaining module 210 may determine the first deflection angle based on a geometric relationship between the planned position and the first deflection position.

In some embodiments, the first deflection angle may be obtained according to the following formula (6):

$$\cos \alpha = z_c D_x / \sqrt{x_c^2 + z_c D_x^2} \tag{6}$$

where $z_c$ is an intersection of the target tumor layer and the Z-axis, $z_c D_x$ is a distance between the first deflection position $D_x$ and $z_c$ in the Z-axis direction, and $x_c$ is a horizontal coordinate of the planned position in the X-axis.

Exemplarily, $z_c D_x = 40$ cm, $x_c = 10$ cm, and then, cos $\alpha = 0.97$.

In some embodiments, the virtual particle source obtaining module 210 may determine the second deflection angle based on the geometric relationship between the planned position and the second deflection position.

In some embodiments, the second deflection angle may be obtained according to the following formula (7)

$$\cos \beta = z_c D_y / \sqrt{y_c^2 + z_c D_y^2} \tag{7}$$

where $z_c D_y$ is a distance between the second deflection position $D_y$ and $z_c$ in the Z-axis direction, and $y_c$ is a vertical coordinate of the planned position in the Y-axis.

Exemplarily, $z_c D_y = 20$ cm, $y_c = 15$ cm, and then, cos $\beta = 0.8$.

An initial velocity may be a unit velocity vector of a particle on the sampling cross-section. In some embodiments, the virtual particle source obtaining module 210 may determine a corresponding initial velocity based on an initial exit angle of a particle.

Specifically, in some embodiments, the virtual particle source obtaining module 210 may determine an initial angle of a particle motion direction (i.e., a direction of the initial velocity) deviated from the Z-axis based on initial angles of the particle motion direction (i.e., the direction of the initial velocity) respectively deviated from the X-axis and the Y-axis.

In some embodiments, the initial angle that the initial velocity is deviated from the Z-axis may be determined according to the following formula (8):

$$v^2 = (|v|*\cos \gamma)^2 + (|v|*\cos \delta)^2 + (|v|*\cos \varepsilon)^2 \tag{8}$$

where v is an initial velocity, $|v|$ is a value of the initial velocity, satisfying $v^2 = |v| = 1$; $\gamma$, $\delta$ and $\varepsilon$ are initial angles that the initial velocity is deviated from the X-axis, the Y-axis and the Z-axis, respectively.

As an example, the virtual particle obtaining module 210 may calculate the initial exit angle $\varepsilon = 31°$ of the initial velocity of the particle A deviated from the Z-axis based on the initial exit angle $\gamma = 70°$ of the initial velocity of the particle A deviated from the X-axis and the initial exit angle $\delta = 60°$ of the initial velocity of the particle A deviated from the Y-axis.

Further, in some embodiments, the virtual particle obtaining module 210 may obtain an initial velocity based on the initial exit angles of the initial velocity of the particle A deviated from the Z-axis, the X-axis and the Y-axis respectively.

Continuing with the above example, the initial velocity of the particle A satisfies $v_A = (\cos 70°, \cos 60°, \cos 31°) = (0.34, 0.50, 0.86)$.

A first velocity may be a unit velocity vector of the particle after the particle passes through the first magnetic field.

In some embodiments, the virtual particle source obtaining module 210 may determine the first velocity based on a first deflection angle. In some embodiments, the first velocity may be determined according to the following formula (9):

$$\begin{cases} v_x' = v_z \cdot \sin\alpha + v_x \cdot \cos\alpha \\ v_y' = v_y \\ v_z' = v_z \cdot \cos\alpha - v_x \cdot \sin\alpha \end{cases} \tag{9}$$

where $v_x'$, $v_y'$ and $v_z'$ are velocity components of the first velocity on the X-axis, Y-axis, and Z-axis, respectively, $v_x$, $v_y$ and $v_z$ are velocity components of the initial velocity of the particle on the X-axis, Y-axis, and Z-axis, respectively, and a is the first deflection angle.

As an example, the virtual particle source obtaining module 210 may obtain the first velocity $v_A'=(0.54, 0.5, 0.76)$ of the particle A based on the initial velocity $v_A=(0.34, 0.50, 0.86)$ and $\cos \alpha=0.97$.

A second velocity may be a unit velocity vector of the particle after the particle passes through the second magnetic field.

In some embodiments, the virtual particle source obtaining module 210 may determine the second velocity based on the second deflection angle to obtain the deflected particle. In some embodiments, the second velocity may be determined according to the following formula (10):

$$\begin{cases} v_x'' = v_x' \\ v_y'' = v_z' \cdot \sin\beta + v_y' \cdot \cos\beta \\ v_z'' = v_z' \cdot \cos\beta - v_y' \cdot \sin\beta \end{cases} \tag{10}$$

where $v_x''$, $v_y''$ and $v_z''$ are velocity components of the second velocity on the X-axis, Y-axis and Z-axis, respectively, $v_x'$, $v_y'$ and $v_z'$ are velocity components of the first velocity on the X-axis, Y-axis and Z-axis, respectively, and $\beta$ is the second deflection angle.

As an example, the virtual particle source obtaining module 210 may obtain the second velocity $v_A''=(0.54, 0.84, 0.32)$ of the particle A based on the first velocity $v_A'=(0.54, 0.5, 0.76)$ and $\cos \beta=0.8$.

In the step 320, one or more of the range modulator, the beam limiting hole, and the exit window are modeled based on the physical properties of the range modulator, the beam limiting hole and the exit window, respectively, to obtain one or more of a range modulator model, a beam limiting hole model, and an exit window model. Specifically, the step 320 may be performed by the modeling module 220. It can be understood that in some embodiments, the range modulator, the beam limiting hole, and the exit window are simultaneously modeled such that all of the range modulator model, the beam limiting hole model, and the exit window model can be obtained.

As shown in FIG. 4, after flowing through the scanning magnet 410, and the particle beam passes through the range modulator 420, the beam limiting hole 430, and the exit window 440 sequentially.

The range modulator 420 may be a device that modulates the range of the particle beam by modulating the longitudinal energy value of the particle beam.

As can be seen from the above description, the active scanning method can divide the tumor into a plurality of layers. In some embodiments, the range modulator may adjust the particle beam to different energy values such that particle beams with different ranges may reach the tumor layers at different depths.

In some embodiments, the range modulator may include multiple layers (e.g., 2 to 18 layers) of absorption medium. As shown in FIG. 4, the range modulator 420 may include six layers of absorption medium.

In some embodiments, a material of the absorption medium may include, but is not limited to, a metal such as copper, a metalloid such as boron, and/or plastic such as methyl methacrylate, etc.

In some embodiments, the thicknesses of the multiple layers of the absorption medium may be different. For example, the range modulator may include six layers of absorption medium and the thicknesses of the layers may be 0.5 cm, 1 cm, 2 cm, 3 cm, 4 cm, and 5 cm, respectively.

In some embodiments, the multiple layers of absorption medium may have the same thickness. For example, the range modulator may include six layers of absorption medium and each layer has a thickness of 1 cm.

In some embodiments, there may exist an interval among the multiple layers of absorption medium. In some embodiments, the interval among the multiple layers of absorption medium is air. As shown in FIG. 4, in the range modulator 420, the intervals among the six layers of absorption medium with a thickness of 1 cm is air. It should be noted that since the influence of air on the particle energy attenuation and scattering may be negligible, in some embodiments, an air region in the treatment head may be simplified as a vacuum region for processing.

In some embodiments, the range modulator may adjust the longitudinal energy value of the particle beam by inserting or removing one or more layers of absorption medium. As an example, as shown in FIG. 4, the deflected particle beam passes through the range modulator, and the six layers of absorption medium in the range modulator 420 can absorb the energy of the particle beam so that the range of the particle beam can reach the first tumor layer (not shown).

Figure 6:
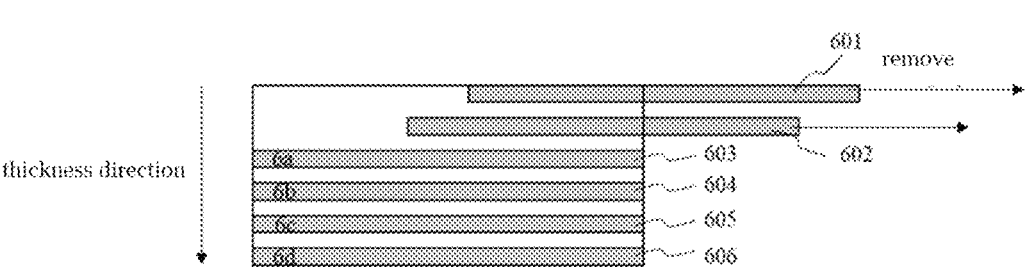
FIG. 6 is an exemplary schematic diagram of a range modulator model according to some embodiments of the present disclosure.

FIG. 6 is an exemplary schematic diagram of a range modulator model according to some embodiments of the present disclosure. As shown in FIG. 6, the first layer absorption medium 601 and the second layer absorption medium 602 are removed from the six layers of absorption medium of the range modulator, so that the absorption medium in the range modulator that absorbs the energy of the particle beam can be reduced. The energy of the particle beam after the particle beam passes through the range modulator is thus increased, and accordingly, the range of the particle beam can reach the sixth tumor layer (not shown).

The range modulator model may be a simulation of physical properties of the range modulator. In some embodiments, the physical properties of the range modulator may include a structure, a dimension, and an absorption medium property of the range modulator, etc.

The structure of the range modulator may include the number of absorption medium layers, e.g., six layers. The dimension of the range modulator may include the thickness of an absorption medium layer, e.g., 2 cm. The absorption medium property of the range modulator may include a density of the absorption medium, e.g., the density of methyl methacrylate is 0.944 g/cm$^3$.

In some embodiments, the modeling module 220 may divide the range modulator into at least one grid based on the physical property of the range modulator, to obtain a range modulator model. A first grid may be a modeling unit of the range modulator model. Specifically, in some embodiments, the modeling module 220 may divide each layer of the range modulator into a first grid in the thickness direction of the range modulator in the Z-axis as shown in FIG. 4, based on the structure, dimension, and absorption medium property of the range modulator. The thickness direction of the range modulator is the same as the direction of motion of the deflected particle beam.

As shown in FIG. 6, four layers of absorption media 603, 604, 605, and 606 are divided into four first grids 6a, 6b, 6c and 6d with a thickness of 2 cm and a density of 0.944 g/cm$^3$, respectively, in the thickness direction of the range modulator.

Since there is no need to compute the energy deposition of particles in the range modulator model, in some embodiments of the present disclosure, dividing each layer in the range modulator into a first grid simplifies the range modulator model and improves modeling efficiency and simulation efficiency.

The beam limiting hole 430 may be a device configured to modify a cross-sectional shape of the particle beam.

Figures 7, 8:
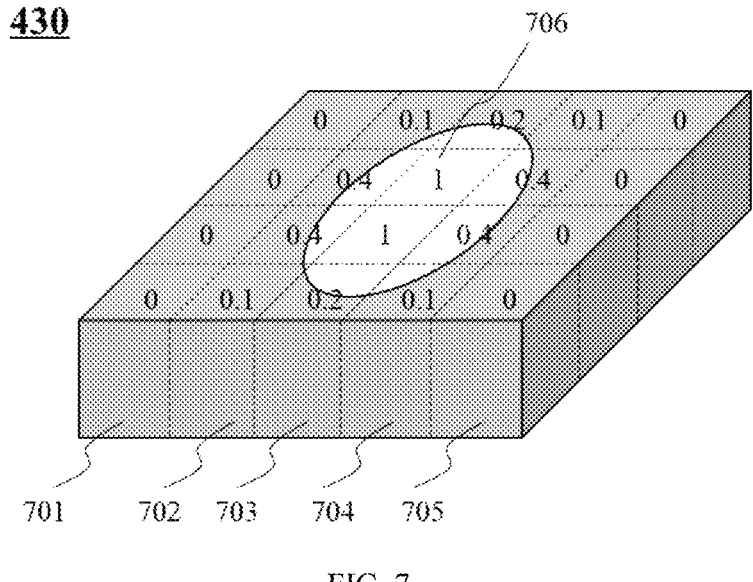
FIG. 7 is an exemplary schematic diagram of a beam limiting hole model according to some embodiments of the present disclosure.
FIG. 8 is an exemplary schematic diagram of a simulated physical process that occurs when deflected particles pass through a range modulator model according to some embodiments of the present disclosure.

In some embodiments, the beam limiting hole 430 may include an occlusion region and a non-occlusion region. FIG. 7 is an exemplary schematic diagram of a beam limiting hole model according to some embodiments of the present disclosure. As shown in FIG. 7, the beam limiting hole may include an occlusion region (gray region) and a non-occlusion region (white region).

In some embodiments, the occlusion region may prevent the particle beam from passing through. In some embodiments, a material of the occlusion region may include, but is not limited to, a nickel alloy, etc.

In some embodiments, the non-occlusion region may be a hollow region allowing the particle beam to pass through. In some embodiments, the shape of the non-occlusion region may be determined based on the shape of the cross-section of a target region of the irradiation field. As shown in FIG. 7, the shape of the non-occlusion region is ellipse, which allows the shape of the cross-section of the particle beam passing through the beam limiting hole to be ellipse, so that the shape of the cross-section of the target region of the irradiation field is ellipse.

The beam limiting hole model may be a simulation of the physical property of the beam limiting hole. In some embodiments, the physical property of the beam limiting hole may include a shape, a dimension, and/or a material property of the beam limiting hole, etc.

The shape of the beam limiting hole may include a shape of a non-occlusion region of the beam limiting hole, such as an ellipse. The dimension of the beam limiting hole may include a length, a width, and a thickness of the beam limiting hole, such as a dimension of 20 cm×16 cm×3 cm. The material property of the beam limiting hole may include a material density, for example, the material of the beam limiting hole is polytetrafluoroethylene with a corresponding density of 2.2 g/cm$^3$.

In some embodiments, the modeling module 220 may divide the beam limiting hole into at least one grid based on the physical property of the beam limiting hole to obtain the beam limiting hole model. A third grid may be a modeling unit of the beam limiting hole model. In some embodiments, the modeling module 220 may divide the beam limiting hole into a plurality of third grids on the cross-section of the beam limiting hole based on the shape, dimension, and/or the material property of the beam limiting hole. The cross-section of the beam limiting hole is perpendicular to the direction of motion of the deflected particle beam, i.e., perpendicular to the Z-axis and parallel to the X-Y plane, as shown in FIG. 4.

As shown in FIG. 7, the modeling module 220 may divide the beam limiting hole into 5×4×1 third grids with a dimension of 4 cm×4 cm×3 cm on the cross-section of the beam limiting hole.

A flux value can indicate an occlusion rate of the third grid to the deflected particle. In some embodiments, a higher flux value indicates a lower occlusion rate. For example, a flux value ω of 1 indicates that the third grid has an occlusion ratio of 0 to the deflected particle, and a flux value ω of 0 indicates that the third grid has an occlusion ratio of 1 to the deflected particle.

In some embodiments, the modeling module 220 may determine a flux value corresponding to each of the plurality of third grids based on the shape of the cross-section of the beam limiting hole. Specifically, in some embodiments, the modeling module 220 may determine a flux value corresponding to each third grid based on a ratio of an area of the non-occlusion region to an area of the occlusion region in each third grid.

For example, as shown in FIG. 7, among the third grids in the first row, the third grids 701 and 705 are completely occlusion regions, and the corresponding flux value is 0. The ratio of the area of the non-occlusion region to the area of the occlusion region in each of the third grids 702 and 704 is equal to 0.1, and the corresponding flux value is 0.1. The ratio of the area of the non-occlusion region to the area of the occlusion region of the third grid 703 is equal to 0.2, and the corresponding flux value is 0.2. Similarly, the flux values of the third grids in the second row from left to right can be determined to be 0, 0.4, 1, 0.4 and 0, respectively, the flux values of third grids in the third row from left to right are 0, 0.4, 1, 0.4 and 0, respectively, and the flux values of third grids in the fourth row from left to right are 0, 0.1, 0.2, 0.1 and 0, respectively.

Further, in some embodiments, the modeling module 220 may obtain a density value corresponding to each third grid based on the flux value corresponding to each third grid and the material density of the beam limiting hole.

In some embodiments, the modeling module 220 may set a third grid with a flux value of 1 as a vacuum grid, and set a density value of a third grid with a flux value of 0 to be equal to the material density of the beam limiting hole. For example, as shown in FIG. 7, the modeling module 220 may set the density value of the third grids 701 and 705 to be ρ=2.2 g/cm$^3$ and set the third grid 706 as a vacuum grid.

In some embodiments, the modeling module 220 may set a density value of a third grid with a flux value ranging from 0 to 1 to a dynamic density. Specifically, in some embodiments, the modeling module 220 may set a probability that a third grid with a flux value w has a density value of ρ to 1-ω, or set a probability that a third grid with a flux value w is a vacuum grid to w. For example, as shown in FIG. 7, the probabilities of the third grids 702, 703 and 704 with the density value ρ=2.2 g/cm$^3$ are 0.9, 0.8 and 0.9, respectively, and the probabilities of the third grids 702, 703 and 704 which are vacuum grids are 0.1, 0.2 and 0.1, respectively.

Further, a specific value of the dynamic density may be determined based on the simulated physical process of the particle in the beam limiting hole model. For a detailed description regarding the simulated physical process of the particle in the beam limiting hole model, reference may be made to the step 330, which is not repeated herein.

In some embodiments of the present disclosure, a beam limiting hole model is established based on the shape of the beam limiting hole and the material of the beam limiting hole, which can simulate the scattering of the particles in the beam limiting hole, thereby improving the accuracy of the modeling.

The exit window may be an exit for the particle beam.

In some embodiments, a material of the exit window may include, but is not limited to, a titanium film, a polycarbonate, etc.

The exit window model may be a simulation of a physical property of the exit window. In some embodiments, the physical property of the exit window model may include a dimension and/or a material property of the exit window, etc.

The dimension of the exit window may include a thickness of the exit window, e.g., 1 cm. The material property of the exit window may include a density of the material, for example, the density of the titanium film is 4.5 g/cm$^3$.

In some embodiments, the modeling module 220 may divide the exit window into a grid based on the physical property of the exit window. A second grid may be a modeling unit of the exit window model. Specifically, in some embodiments, the modeling module 220 may divide the exit window into a second grid.

As shown in FIG. 4, for example, the modeling module 220 may divide the exit window 440 into a second grid with a thickness of 1 cm and a density of 4.5 g/cm$^3$.

Since it is not required to calculate the energy deposition of the particles in the exit window model, in some embodiments of the present disclosure, the exit window as a whole is divided into a second grid, thereby simplifying the exit window model, and improving the modeling efficiency and the simulation efficiency.

In some embodiments of the present disclosure, the components in the treatment head are separately modeled, so that each model is independent, and accordingly, components can be divided into grids flexibly according to different geometries of the components, thereby improving modeling efficiency and modeling accuracy.

In the step 330, physical processes of the deflected particle in the one or more of the range modulator model, the beam limiting hole model, and the exit window model are simulated. Specifically, the step 330 may be performed by a simulation module 230. It can be understood that in some embodiments, the physical processes of the deflected particle in all of the range modulator model, the beam limiting hole model, and the exit window model are simulated.

A physical process of a deflected particle in a model may include a collision of the deflected particle with an atom in the model, a change in a motion direction and/or an energy loss caused by the collision. A collision path may be a changing path in the motion direction after the particle collides with the atom in the model. The energy loss may be a loss in energy caused by a collision of the particle with the atom in the model.

In some embodiments, the simulation module 230 may simulate the collision path and the energy loss of the deflected particle in the range modulator model based on an arrangement of at least one first grid.

In some embodiments, the energy attenuation and scattering of the deflected particle in the air region of the range modulator may be negligible.

As can be seen from the above description, the treatment head can be regarded as being in a vacuum state. In some embodiments, in the path of the particle from the scanning magnet to the first grid of the range modulator model, the energy attenuation and scattering of the particle caused by the air can be negligible, so that the velocity and energy with which the particle enters the first grid may not change. FIG. 8 is an exemplary schematic diagram of a simulated physical process of a deflected particle in the range modulator model according to some embodiments of the present disclosure. For example, as shown in FIG. 8, the initial energy value of the deflected particle A is 100 MeV, the second velocity is $v_A''=(0.54, 0.84, 0.32)$, and then the energy value of the particle A when entering the first grid 6a is $E_A'=100$ MeV, with the velocity $v_A'=(0.54, 0.84, 0.32)$.

In some embodiments, the simulation module 230 may determine a position at which the particle enters the first grid based on a position of the deflected particle, a position of the first grid, and the second velocity. Continuing with the above example, as shown in FIG. 8, the simulation module 230 may determine the position A' at which the particle enters the first grid based on a current position of the particle A, a distance between an incident plane of the first grid and a current tumor layer in the Z-axis direction, and the direction of the second velocity $v_A''$.

As an example, the initial position of the particle A is (5.12, 4.09), and the distance between the virtual particle source and the current tumor layer in the Z-axis direction is 50 cm, then the current position of the particle A is (5.12, 4.09, 50). Then, the simulation module 230 may determine the position A' at which the particle enters the first grid based on the second velocity $v_A''=(0.54, 0.84, 0.32)$ and the distance of 10 cm between the incident plane of the first grid and the current tumor layer in the Z-axis direction.

As can be seen from the above description, intervals among the plurality of first grids in the range modulator model can be regarded as a vacuum, and the energy attenuation and scattering of the particle by air can be negligible in a path from a first grid to a next first grid. Thus, in some embodiments, the velocity and energy with which the particle enters one first grid are equal to the velocity and energy with which the particle exits a previous first grid. Continuing with the example in FIG. 8, the particle A exits the first grid 6a with the energy $E_A''^2$ and the velocity $v_A''^2$, so that the particle A enters the first grid 6b with the energy $E_A'''^1=E_A''^2$ and the velocity $v_A'''^1=v_A''^2$.

In some embodiments, the simulation module 230 may determine a position and a velocity at which the particle enters one first grid based on the position and velocity at which the particle exits a previous first grid. Continuing with the above example, as shown in FIG. 8, the simulation module 230 may determine the position A''' at which the particle enters the first grid 6b based on the position A'' and the velocity at which the particle exits the first grid 6a.

In some embodiments, the simulation module 230 may simulate the physical process of the deflected particle in each first grid in the range modulator.

In some embodiments, the deflected particle may react with an atom in each first grid in the range modulator in one or more of the following ways: inelastic Coulomb scattering, elastic Coulomb scattering, inelastic nuclear scattering, etc.

The inelastic Coulomb scattering can be an interaction of a particle and an electron outside a nucleus. In some embodiments, the inelastic Coulomb scattering may result in the energy loss of the particle. The elastic Coulomb scattering can be an interaction of a particle and a nucleus. In some embodiments, the elastic Coulomb scattering may change the motion direction of the particle. The inelastic nuclear scattering may be an interaction between a particle and a nucleus. In some embodiments, the inelastic nuclear scattering may produce a secondary particle (e.g., a proton, a neutron, etc.). Accordingly, in some embodiments, an energy loss and/or a change in the motion direction may occur to the deflected particle in each first grid.

In some embodiments, the simulation module 230 may simulate the reaction of the particle in the first grid by, but not limited to, one or more of a Monte Carlo method, a pencil beam algorithm, or a ray tracing algorithm, etc.

As an example, the Monte Carlo method may simulate the reaction of the particle in the first grid based on a picked random number. The Monte Carlo method is a numerical calculation method based on a probability and a statistical theory, which can decompose a transport process of a particle in a medium into a plurality of steps, and solve a result of each step according to the random number picked each time, a particle state, and a database for a cross-section of the medium, until the entire transport process of the particle is completely tracked.

In some embodiments, the simulation module 230 may pick a fifth random number and determine a reaction type of a particle and an atom based on the fifth random number. The simulation module 230 then picks a plurality of different random numbers based on different reaction types, respectively, and determines a reaction position, an energy loss caused by the reaction, a change in the motion direction, and/or a type of a secondary particle generated, etc., based on the plurality of different random numbers.

As an example, the simulation module 230 may determine the reaction type of the particle and the atom as the inelastic Coulomb scattering based on the fifth random number, and further pick a sixth random number to determine a position at which the inelastic Coulomb scattering occurs and pick a seventh random number to determine the energy loss of the particle in the inelastic Coulomb scattering based on the density of the first grid. For example, as shown in FIG. 8, the simulation module 230 may determine the reaction type of the particle A in the first grid 6a as the inelastic Coulomb scattering based on the fifth random number, determine the position of the inelastic Coulomb scattering of the particle A as $P_a$ ( . . . , . . . , . . . ) based on the sixth random number, and determine the energy loss to be 0.5 MeV based on the seventh random number and the density of the first grid of 0.944 $g/cm^3$.

In another embodiment, the simulation module 230 may determine the reaction type of the particle and the atom as the elastic Coulomb scattering based on the fifth random number, and further pick an eighth random number to determine the position at which the elastic Coulomb scattering occurs and pick a ninth random number to determine the motion direction and the energy loss of the particle after the elastic Coulomb scattering based on the density of the first grid. For example, as shown in FIG. 8, the simulation module 230 may determine that the reaction type of the particle A in the first grid 6b to be the elastic Coulomb scattering based on another fifth random number, and determine the position at which the elastic Coulomb scattering of the particle A occurs to be the position Pb based on the eighth random number, and determine that the motion direction of the particle A is changed to $v_{p_b}$ and the energy loss is 0.4 MeV based on the ninth random number and the density of the first grid of 0.944 $g/cm^3$.

As another example, the simulation module 230 may determine the reaction type of the particle and the atom as the inelastic nuclear scattering based on the fifth random number, and further pick a tenth random number to determine the position at which the inelastic nuclear scattering of the particle occurs and pick an eleventh random number to determine a type of a secondary particle generated by the particle in the inelastic nuclear scattering, such as a secondary proton and/or a secondary neutron, etc. For example, as shown in FIG. 8, the simulation module 230 may determine the reaction type of the particle A in the first grid 6c as the inelastic nuclear scattering based on another fifth random number, determine the position at which the inelastic nuclear scattering of the particle A occurs to be the position $P_c$ based on the tenth random number, and determine the type of the secondary particle as a secondary proton and a secondary neutron based on the eleventh random number.

In some embodiments, the simulation module 230 may simulate the secondary particle generated by the deflected particle in the range modulator model. As an example, the simulation module 230 may pick a twelfth random number to determine the energy values of the secondary proton and the secondary neutron, and pick a thirteenth random number to determine the motion directions of the secondary proton and the secondary neutron. For example, as shown in FIG. 8, the simulation module 230 may determine the energy value of the secondary proton F (denoted by a black dot) and the energy value of the secondary neutron G (denoted by a white dot) generated at the position $P_c$ in the first grid 6C to be 85 MeV and 5 MeV, respectively, based on the twelfth random number, and determine the directions of the secondary proton and the secondary neutron as $v_{p_c}^F$ and $v_{p_c}^G$, respectively, based on the thirteenth random number.

In some embodiments, the simulation module 230 may further determine the reaction type of the secondary particle based on a newly picked fifth random number, and continue to pick a plurality of new different random numbers based on the reaction type of the secondary particle and simulate the physical process of the secondary particle.

For example, as shown in FIG. 8, the simulation module 230 may determine the reaction type of the secondary proton F at the position $P_d$ in the first grid 6d to be the inelastic nuclear scattering based on a newly picked fifth random number, determine a coordinate of a position $P_d$ of the inelastic nuclear scattering based on the newly picked tenth random number, and pick the eleventh random number to determine the types of the secondary particles generated by the secondary proton F in the inelastic nuclear scattering to be the secondary proton I and the secondary proton J. Further, the simulation module 230 may simulate the physical processes of the secondary proton I and the secondary proton J.

The first state may be a state of the particle before reacting with the atom. For example, as shown in FIG. 8, the particle A, after entering the first grid 6a, reacts with the atom in the first grid 6a for the first time at the position A' at which the particle A enters the first grid 6a, then the first state of the particle A may be a state when the particle A enters the first grid 6a.

In some embodiments, the first state may include a first energy and a first motion direction. The first energy and the first motion direction may be the energy and the motion direction before the particle reacts with the atom. Continuing with the above example, as shown in FIG. 8, the particle A after deflection enters the first grid 6a through an air region with an energy value of $E_A$=100 MeV, a velocity of $v_A$=(0.54, 0.84, 0.32), and a position of $P_a$( . . . , . . . , . . . ), then the first state of the particle A may include $E_{A'}^1$=100 MeV, $v_{A'}^1$=(0.54, 0.84, 0.32), and $P_a$( . . . , . . . , . . . ).

A second state may be a state after the particle reacts with the atom. In some embodiments, similarly to the first state, the second state may include a second energy and a second motion direction. The second energy and the second motion direction may be the energy and the motion direction after the particle reacts with the atom.

In some embodiments, for each reaction, the simulation module 230 may determine a corresponding second state based on the first state of the particle according to a simulated reaction of the particle with the atom.

Continuing with the above example, as shown in FIG. 8, the simulation module 230 may determine the second state of the particle A to be $E_{A'}^2$=99.5 MeV, $v_{A'}^2$=(0.54, 0.84, 0.32), $P_a$( . . . , . . . , . . . ) based on the first state of the particle A including $E_{A'}^1$=100 MeV, $v_{A'}^1$=(0.54, 0.84, 0.32) and $P_a$( . . . , . . . , . . . ) according to the simulated first reaction of the particle A in the first grid 6a including the way of inelastic Coulomb scattering, the energy loss of 0.5 MeV, the coordinate of the position $P_a$ of the reaction, and the unchanged motion direction.

In some embodiments, after simulating one reaction of the particle in the first grid, the simulation module 230 may simulate the next reaction. Specifically, in some embodiments, the simulation module 230 may determine the second state of the particle in the previous reaction to be the first state of the next reaction.

For example, continuing with FIG. 8, the first state of the particle A in the second reaction in the first grid 6a (at the position $P_d$) may be the second state of the particle A in the first reaction, e.g., $E_{Pd}^1 = E_A'^2 = 99.5$ MeV, $v_{pd}^1 = v_A'^2 = (0.54, 0.84, 0.32)$, and $P_a(\ldots, \ldots, \ldots)$. Further, the simulation module 230 may determine the second state of the particle A in the second reaction including $E_{Pd}^2 = \ldots, v_{pd}^2 = \ldots, P_a(\ldots, \ldots, \ldots)$ based on the first state of the particle A in the second reaction according to the simulated second reaction of the particle A in the first grid 6a.

In some embodiments, the simulation module 230 may determine a position at which the particle exits the first grid based on the thickness of the first grid of the range modulation model. Continuing with the above example, the simulation module 230 may determine, based on the thickness of 2 cm of the first grid 6a, a reaction position A″ at a distance of 2 cm from the first reaction position $P_a$ (or A') in the Z-axis direction as the position at which the particle A exits the first grid 6a.

In some embodiments, the simulation module 230 may determine whether the secondary particle is able to pass through the range modulator model.

As can be seen from the above description, in some embodiments, the inelastic nuclear scattering may occur between the particle and atom, and a secondary particle is generated. In some embodiments, the simulation module 230 may determine, based on an energy threshold, whether the generated secondary particle is able to pass through the range modulator model.

The energy threshold may be a threshold for determining whether the secondary particle is able to pass through the range modulator model. In some embodiments, the simulation module 230 may determine a corresponding energy threshold based on a vertical distance from a position at which the secondary particle is generated to an exit surface of the range modulator model. Specifically, the simulation module 230 may calculate the minimum energy required for the shortest distance (i.e., the vertical distance) from the position at which the secondary particle is generated to the exit surface of the range modulator model as the corresponding energy threshold. It will be appreciated that the greater the vertical distance from the position at which the secondary particle is generated to the exit surface of the range modulator model, the greater the energy threshold.

For example, as shown in FIG. 8, the vertical distance from the position $P_c$ in the first grid 6c to the exit surface MM' of the range modulator model is $D_{Pc}$, and then the minimum particle energy $E_{Pc}$ required for the vertical distance $D_{Pc}$ can be calculated to be equal to 30 MeV, as the energy threshold corresponding to the position $P_c$. The vertical distance from the position $P_a$ in the first grid 6d to the exit surface MM' of the range modulator model is $D_{Pd}$, and then the minimum particle energy $E_{Pd}$ required for the vertical distance $D_{Pd}$ can be calculated to be equal to 20 MeV, as the energy threshold corresponding to the position $P_a$.

In some embodiments, when the energy value of the secondary particle at the position at which the secondary particle is generated is less than the corresponding energy threshold, the simulation module 230 may then determine that the secondary particle is not able to pass through the range modulator model. For example, when the energy 5 MeV of the secondary neutron G at the position $P_c$ is less than the energy threshold $E_{Pc} = 30$ MeV, it is determined that the secondary neutron G is not able to pass through the range modulator model.

In some implementations, when the energy value of the secondary particle at the position at which the secondary particle is generated is greater than the corresponding energy threshold, the simulation module 230 may determine that the secondary particle is able to pass through the range modulator model. For example, when the energy value of the secondary proton F of 85 MeV at the position $P_c$ is greater than the energy threshold $E_{Pc} = 30$ MeV, it is determined that the secondary proton F is able to pass through the range modulator model.

In some embodiments, the simulation module 230 may store the state of the secondary particle in response to the passage of the secondary particle through the range modulator model. The state of the secondary particle may include position information, energy information, and motion direction information of the secondary particle. Secondary particles that do not pass through the range modulator can be excluded from consideration.

Continuing with the above example, as shown in FIG. 8, the simulation module 230 may store the state of the secondary particle F after passing through the range modulator model in order to simulate the physical process of the secondary particle F passing through the beam limiting hole model based on the stored state of the secondary particles F.

In some embodiments of the present disclosure, only states of the secondary particles passing through the range modulator are stored, so that the calculation can be simplified and the simulation efficiency can be improved.

In some embodiments, the simulation module 230 may simulate the collision path and energy loss of the deflected particle in the beam limiting hole model based on the density value corresponding to each third grid.

In some embodiments, the energy attenuation and scattering of the deflected particle occurring in the air region between the range modulator model exited by the particle and the beam limiting hole model entered by the particle is negligible. Thus, the velocity and energy value of the particle entering the beam limiting hole model may not change. For example, as shown in FIG. 8, the velocity and energy value of the secondary proton I exiting the range modulator model are $v_{MM'}^2$ and $E_{MM'}^2$ respectively, and the velocity and energy value of the secondary proton I entering the beam limiting hole model are $v_I^1 = v_{MM'}^2$ and $E_I^1 = E_{MM'}^2$ respectively.

Figure 9:
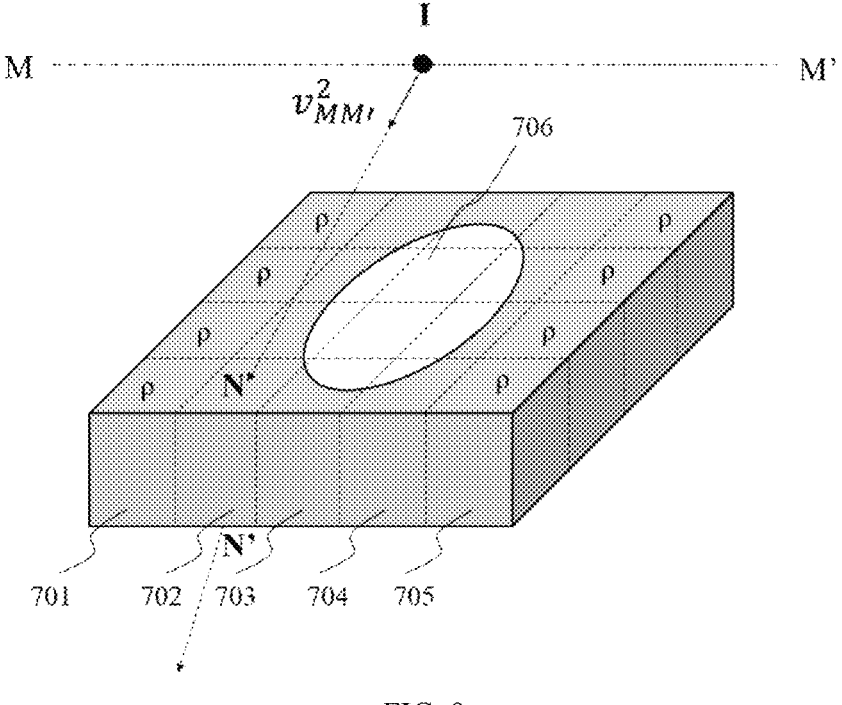
FIG. 9 is an exemplary schematic diagram of a simulated physical process that occurs when deflected particles pass through a beam limiting hole model according to some embodiments of the present disclosure.

In some embodiments, the simulation module 230 may determine a position and a third grid at which the particle enters the beam limiting hole model based on the position and velocity at which the deflected particle exits the range modulator model and the position of the beam limiting hole model. FIG. 9 is an exemplary schematic diagram of a simulated physical process of a deflected particle in a beam limiting hole model according to some embodiments of the present disclosure. As shown in FIG. 9, the simulation module 230 may determine the position N and the third grid 702 at which the secondary proton I enters the beam limiting hole model based on the position $P_{MM'}^2$ (not shown) and the velocity $v_{MM'}^2$ at which the secondary proton I exits the range modulator model.

Similar to the range modulator model, in some embodiments, the simulation module 230 may simulate the reaction of the particle in the third grid by, but not limited to, one or more of a Monte Carlo method, a pencil beam algorithm, or a ray tracing algorithm, etc.

Continuing with the Monte Carlo method as an example, the simulation module 230 may pick a fourteenth random number and determine a density value corresponding to the third grid in which the particle enters based on the fourteenth random number and a probability of the density value corresponding to the third grid. For a detailed description of the probability of the density value corresponding to the third grid, reference can be made to the step 320 and related description thereof, which will not be repeated herein.

For example, continuing with the above example, the probability that the density value of the third grid 702 is $\rho=2.2$ g/cm$^3$ is equal to 0.9, and the simulation module 230 determines the density value of the third grid 702 as $\rho=2.2$ g/cm$^3$ based on the fourteenth random number and the probability of 0.9.

Further, in some embodiments, the simulation module 230 may simulate the reaction of the particle with the atom in the third grid based on the thickness and density values of the third grid. For the detailed description of the reaction of the particle with the atom in the third grid, reference can be made to the first grid, which will not be repeated herein.

For example, the secondary proton I reacts with a plurality of atoms in the third grid, with no secondary particle generated, then the velocity and energy with which the secondary proton I exits the third grid are $v_I^2$ and $E_I^2$ respectively, and the position at which the secondary proton I exits the third grid is N'.

As can be seen from the above description, in some embodiments, the third grid may be set to be a vacuum, for example, the third grid 706. In some embodiments, the deflected particle may not collide with any atom and lose energy in the third grid set as a vacuum. Accordingly, the velocity and energy with which the particle enters the third vacuum grid may not change.

In some embodiments, the simulation module 230 may simulate the collision path and energy loss of the deflected particle in the exit window model.

In some embodiments, the energy attenuation and scattering of the deflected particle occurring in the air region between the beam limiting hole model and the exit window model is negligible. Accordingly, the velocity and energy with which the particle enters the exit window model may not change. For example, the velocity and energy with which the secondary proton I exits the beam limiting hole model are $v_I^2$ and $E_I^2$ respectively, and the velocity and energy with which the secondary proton I enters the exit window model are $v_{I'}^1=v_I^2$ and $E_{I'}^1=E_I^2$ respectively.

In some embodiments, the simulation module 230 may determine the position at which the particle enters the exit window model based on the position and velocity with which the deflected particle exits the beam limiting hole model and the position of the exit window model. For example, the simulation module 230 may determine the position at which the secondary proton I enters the exit window model based on the position N', the velocity $v_I^2$ and the direction at which the secondary proton I exits the beam limiting hole model.

Further, in some embodiments, the simulation module 230 may simulate the reaction of the particle with the atom in the exit window model based on the thickness and density value of the exit window model. For the detailed description of the reaction of the particle with the atom in the exit window model, reference can be made to the first grid, which will not be repeated here.

For example, the secondary proton I reacts with a plurality of atoms in the exit window model, with no secondary particle generated, then the velocity and energy with which the secondary proton I exits the exit window model are $v_{I'}^2$, $E_{I'}^2$, respectively, and the position is K.

In some embodiments of the present disclosure, the treatment head is separately modeled, so that the treatment head model is independent of the model body, and even if the positioning of the model is changed, there is no need to repeat the modeling of the treatment head, accordingly the efficiency of the modeling can be improved.

Further, in some embodiments, the simulation module 230 may simulate a transport of a particle in a target object to determine a dose distribution result in the target object. In some embodiments, the target object may include, but is not limited to, a human body, an organ, an organism, an object, a model body, a region of interest, a lesion portion, and/or a tumor, etc.

In some embodiments, the simulation module 230 may determine the position and velocity at which the particle reaches a scanning object based on the position and velocity at which the particle exits the exit window model, and then simulate the transport process of the particle in the target object using the Monte Carlo method to determine the dose distribution result in the target object.

In some embodiments, the simulation module 230 may optimize the treatment plan based on the dose distribution result in the target object. In some embodiments, the simulation module 230 may optimize the treatment plan with an optimization model based on the dose distribution result to determine an optimized dose distribution result.

In some embodiments, the optimization model may include an algorithm model and/or a machine learning model. In some embodiments, the algorithm model may include, but is not limited to, a primary radiation dose and scattered radiation dose separation model, a convolution model, and a Monte Carlo algorithm model, etc. In some embodiments, the machine learning model may include, but is not limited to, a Convolutional Neural Networks (CNN) model, a Recurrent Neural Network (RNN) model, a Long Short Term Memory Network (LSTM) model, etc.

In some embodiments, the simulation module 230 may determine a dose verification result based on a comparison between the simulated dose distribution result to a measured dose distribution result.

The present disclosure further provides a particle transport simulation device, which includes at least one processor and at least one memory storing computer instructions therein. The at least one processor, when executing at least a part of the computer instructions, performs a method for simulating particle transport according to any of the embodiments described above.

Figure 10:
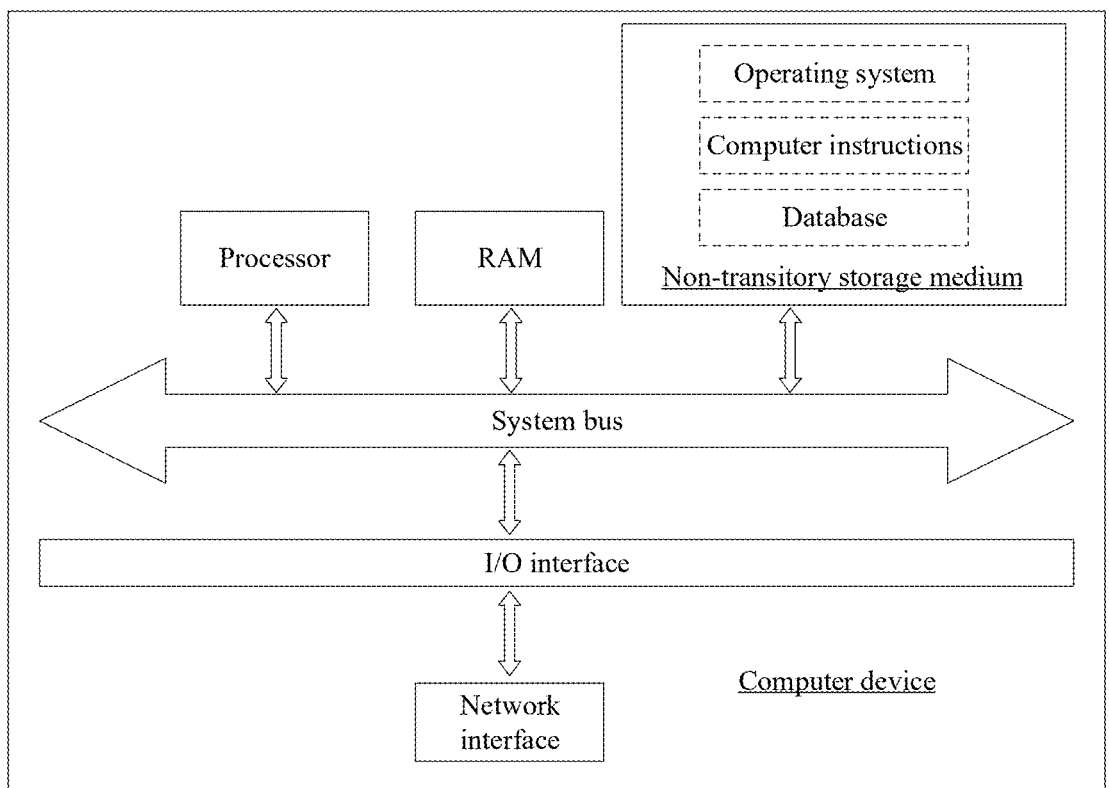
FIG. 10 is a schematic diagram of an internal structure of a computer device according to some embodiments of the present disclosure.

In some embodiments, the particle transport simulation device is a computer device. The computer device can be either a terminal or a server, as shown in FIG. 10 for its internal structure. The computer device includes a processor, memory, and network interface connected via a system bus. The processor of the computer device is responsible for providing computation and control capabilities. The memory of the computer device comprises non-transitory storage medium and random access memory (RAM). The non-transitory storage medium stores the operating system, computer instructions, and databases. The RAM provides an environment for the execution of the operating system and computer instructions stored in the non-transitory storage medium. Optionally, the computer device may also include a display and an input device.

The present disclosure further provides a non-transitory computer-readable storage medium storing instructions that, when executed by one or more processors, cause the one or more processors to perform a method for simulating particle transport according to various embodiments of the present disclosure.

The advantages of the embodiments of the present disclosure may include, but are not limited to: (1) The treatment head is separately modeled. There is no need to repeat modeling of the treatment head even if the positioning of the model body changes, thereby improving the efficiency of the modeling; (2) The virtual particle source is obtained based on a double Gaussian distribution with covariance so that the virtual particle source is capable of being adapted to various shapes of beam spots of a plurality of particle beams, thereby improving the adjustment freedom of the virtual particle source; (3) The modeling is performed based on the real structures of the range modulator, the beam limiting hole, and the exit window, to obtain the range modulator model, the beam limiting hole model, and the exit window model, so that the modeling accuracy is improved; (4) Each layer of the range modulator is divided into one gird and the exit window as a whole is divided into one gird, so that the models are simplified and the modeling efficiency and the simulation efficiency can be improved; (5) The beam limiting hole model is established based on the shape and material of the beam limiting hole, so that scattering of the particle in the beam limiting hole can be simulated, and the modeling accuracy can be improved; (6) Each component of the treatment head is separately modeled so that each model is independent, so that grids can be set flexibly according to different geometrical structures of the components, thereby improving the modeling efficiency and accuracy; (7) A secondary particle that is not able to pass through the range modulator is removed, thereby simplifying the calculation and improving the simulation efficiency. It should be noted that different embodiments may have different advantages. In different embodiments, the advantages may be any one or more of the above, or may be any other advantages that may be obtained.

The basic concept is described above, it will be apparent to those skilled in the art that the above detailed disclosure is by way of example only and does not constitute a limitation to the specification. Although not explicitly described herein, those skilled in the art can make various modifications, improvements, and transformations. Such modifications, improvements, and transformations are suggested in this specification, so such modifications, improvements, and transformations still fall within the spirit and scope of the exemplary embodiments in the present disclosure At the same time, the specification uses specific words to describe embodiments of the disclosure. For example, "one embodiment", "an embodiment", and/or "some embodiments" means a feature, a structure, or a characteristic associated with at least one embodiment of the disclosure. Therefore, it should be emphasized and noted that reference in this disclosure to "an embodiment" or "one embodiment" or "an alternative embodiment" two or more times at different positions does not definitely refer to the same embodiment. In addition, certain features, structures, or characteristics in one or more embodiments of the present disclosure may be combined as appropriate.

Furthermore, unless expressly stated in the claims, the order of the processing elements and sequences described in this disclosure, the use of numeric letters, or the use of other names are not intended to limit the order of the procedure and method of the disclosure. While some embodiments of the disclosure are presently considered to be useful by way of example in the foregoing disclosure, it should be appreciated that such detail is for illustrative purposes only, and that the appended claims are not limited to the disclosed embodiments. Rather, the claims are intended to cover all modifications and equivalent combinations consistent with the spirit and scope of the embodiments of the disclosure. For example, although the system components described above may be implemented by a hardware device, they may also be implemented only by a software solution, such as the installation of the described system on an existing server or mobile device.

Similarly, it should be noted that in the foregoing description of the embodiments of the present disclosure, various features may sometimes be incorporated in one embodiment, one drawing, or in the description thereof, in order to simplify the description of the present disclosure and thereby facilitate an understanding of one or more embodiments of the present disclosure. However, such a disclosure manner does not imply that the subject matter of the specification requires more features than those mentioned in the claims. Indeed, the features of an embodiment are less than all features of individual embodiments disclosed above.

In some embodiments, as for the numerical parameters, the specified valid digits should be considered and a general digit retention method is employed. Although the numerical ranges and parameters for determining the breadth of the range in some embodiments of the present disclosure are approximations, in specific embodiments, such numerical values may be set as accurate as possible within the feasible range.

Finally, it should be appreciated that the embodiments described in the specification are merely for illustrating the embodiments of the disclosure. Other transformations are possible within the scope of the disclosure. Thus, by way of example and not limitation, alternative configurations in the embodiments of the present disclosure may be regarded as being consistent with the teachings of the present disclosure. Accordingly, the embodiments of the disclosure are not limited to the embodiments explicitly introduced and described and described herein.

What is claimed is:

1. A method for simulating a particle transport, comprising:

obtaining a virtual particle source;

simulating a deflection of the virtual particle source under a magnetic field to obtain a deflected particle;

modeling one or more of a range modulator, a beam limiting hole, and an exit window based on physical properties of the range modulator, the beam limiting hole, and the exit window, respectively, to obtain one or more of a range modulator model, a beam limiting hole model, and an exit window model; and simulating physical processes of the deflected particle in the one or more of the range modulator model, the beam limiting hole model, and the exit window model, respectively.

2. The method according to claim 1, wherein the obtaining the virtual particle source comprises:

obtaining an initial energy value, an initial position, and an initial angle of the virtual particle source based on a probability distribution function.

3. The method according to claim 2, wherein the obtaining the virtual particle source further comprises:

obtaining an initial position distribution of the virtual particle source based on a double Gaussian distribution without a covariance or a double Gaussian distribution with a covariance, the covariance representing a correlation between an initial position of a particle of the virtual particle source on an X-axis and an initial position of the particle of the virtual particle source on a Y-axis.

4. The method according to claim 1, wherein the modeling the one or more of the range modulator, the beam limiting hole, and the exit window based on the physical properties of the range modulator, the beam limiting hole, and the exit window, respectively, to obtain the one or more of the range modulator model, the beam limiting hole model, and the exit window model comprising:

modeling the range modulator, the beam limiting hole, and the exit window based on the physical properties of the range modulator, the beam limiting hole, and the exit window, respectively, to obtain the range modulator model, the beam limiting hole model, and the exit window model, and wherein the simulating the physical processes of the deflected particle in the one or more of the range modulator model, the beam limiting hole model, and the exit window model, respectively, comprising:

simulating the physical processes of the deflected particle in the range modulator model, the beam limiting hole model, and the exit window model, respectively.

5. The method according to claim 4, wherein the modeling the range modulator, the beam limiting hole, and the exit window based on the physical properties of the range modulator, the beam limiting hole, and the exit window, respectively, to obtain the range modulator model, the beam limiting hole model, and the exit window model comprises:

dividing the range modulator, the beam limiting hole, and the exit window into at least one grid based on the physical properties of the range modulator, the beam limiting hole, and the exit window, respectively, to obtain the range modulator model, the beam limiting hole model, and the exit window model.

6. The method according to claim 5, wherein the modeling the range modulator, the beam limiting hole, and the exit window based on the physical properties of the range modulator, the beam limiting hole, and the exit window, respectively, to obtain the range modulator model, the beam limiting hole model, and the exit window model further comprises:

dividing each layer of the range modulator into a first grid in a thickness direction of the range modulator based on at least one of a structure, a dimension of the range modulator, or a property of an absorption material of the range modulator.

7. The method according to claim 6, wherein the modeling the range modulator, the beam limiting hole, and the exit window based on the physical properties of the range modulator, the beam limiting hole, and the exit window, respectively, to obtain the range modulator model, the beam limiting hole model, and the exit window model further comprises:

dividing the exit window into a single second grid.

8. The method according to claim 6, wherein the simulating the physical processes of the deflected particle in the range modulator model, the beam limiting hole model, and the exit window model, respectively comprises:

simulating reactions of the deflected particle in the first grid by one or more of a Monte Carlo method, a pencil beam algorithm, or a ray tracing algorithm.

9. The method according to claim 4, wherein the modeling the range modulator, the beam limiting hole, and the exit window based on the physical properties of the range modulator, the beam limiting hole, and the exit window, respectively, to obtain the range modulator model, the beam limiting hole model, and the exit window model comprises:

dividing the beam limiting hole into a plurality of third grids on a cross-section of the beam limiting hole based on at least one of a shape, a dimension, or a material property of the beam limiting hole.

10. The method according to claim 9, wherein the modeling the range modulator, the beam limiting hole, and the exit window based on the physical properties of the range modulator, the beam limiting hole, and the exit window, respectively, to obtain the range modulator model, the beam limiting hole model, and the exit window model further comprises:

determining a flux value corresponding to each of the plurality of third grids on the cross-section of the beam limiting hole based on a shape of the cross-section of the beam limiting hole, the flux value indicating an occlusion rate of one of the plurality of third grids against the deflected particle; and obtaining a density value corresponding to each of the plurality of third grids on the cross-section of the beam limiting hole based on the flux value corresponding to each third grid of the plurality of third grids on the cross-section of the beam limiting hole and a material density of the beam limiting hole.

11. The method according to claim 10, wherein the determining the flux value corresponding to each of the plurality of third grids on the cross-section of the beam limiting hole based on the shape of the cross-section of the beam limiting hole comprises determining the flux value based on a ratio of an area of a non-occlusion region to an area of an occlusion region of each third grid of the plurality of third grids on the cross-section of the beam limiting hole.

12. The method according to claim 10, wherein the simulating the physical processes of the deflected particle in the range modulator model, the beam limiting hole model, and the exit window model, respectively comprises:

simulating a collision path and an energy loss of the deflected particle in the beam limiting hole model based on the density value corresponding to each third grid of the plurality of third grids on the cross-section of the beam limiting hole.

13. The method according to claim 4, wherein the simulating the physical processes of the deflected particle in the range modulator model, the beam limiting hole model, and the exit window model, respectively comprises:

simulating a secondary particle generated by the deflected particle in the range modulator model;

determining whether the secondary particle is able to pass through the range modulator model; and storing a state of the secondary particle in response to a passage of the secondary particle through the range modulator model.

14. The method according to claim 1, further comprising:

obtaining a dose distribution simulation result based on a simulation; and determining a treatment plan based on the dose distribution simulation result.

15. A particle transport simulation device, comprising:

at least one processor and at least one memory storing computer instructions therein, wherein the at least one processor, when executing at least a part of the computer instructions, performs a method for simulating a particle transport, the method comprising:

obtaining a virtual particle source;

simulating a deflection of the virtual particle source under a magnetic field to obtain a deflected particle;

modeling one or more of a range modulator, a beam limiting hole, and an exit window based on physical properties of the range modulator, the beam limiting hole, and the exit window, respectively, to obtain one or more of a range modulator model, a beam limiting hole model, and an exit window model; and simulating physical processes of the deflected particle in the one or more of the range modulator model, the beam limiting hole model, and the exit window model, respectively.

16. The particle transport simulation device according to claim 15, wherein the modeling the one or more of the range modulator, the beam limiting hole, and the exit window based on the physical properties of the range modulator, the beam limiting hole and the exit window, respectively, to obtain the one or more of the range modulator model, the beam limiting hole model, and the exit window model comprising:

modeling the range modulator, the beam limiting hole, and the exit window based on the physical properties of the range modulator, the beam limiting hole, and the exit window, respectively, to obtain the range modulator model, the beam limiting hole model, and the exit window model, and wherein the simulating the physical processes of the deflected particle in the one or more of the range modulator model, the beam limiting hole model, and the exit window model, respectively, comprising:

simulating the physical processes of the deflected particle in the range modulator model, the beam limiting hole model, and the exit window model, respectively.

17. The particle transport simulation device according to claim 16, wherein the modeling the range modulator, the beam limiting hole, and the exit window based on the physical properties of the range modulator, the beam limiting hole, and the exit window, respectively, to obtain the range modulator model, the beam limiting hole model, and the exit window model comprises:

dividing the range modulator, the beam limiting hole, and the exit window into at least one grid based on the physical properties of the range modulator, the beam limiting hole, and the exit window, respectively, to obtain the range modulator model, the beam limiting hole model, and the exit window model.

18. The particle transport simulation device according to claim 17, wherein the modeling the range modulator, the beam limiting hole, and the exit window based on the physical properties of the range modulator, the beam limiting hole, and the exit window, respectively, to obtain the range modulator model, the beam limiting hole model, and the exit window model further comprises:

dividing each layer of the range modulator into a first grid in a thickness direction of the range modulator based on at least one of a structure, a dimension of the range modulator, or a property of an absorption material of the range modulator;

dividing the exit window into a single second grid; and dividing the beam limiting hole into a plurality of third grids on a cross-section of the beam limiting hole based on at least one of a shape, a dimension, or a material property of the beam limiting hole.

19. The particle transport simulation device according to claim 16, wherein the simulating the physical processes of the deflected particle in the range modulator model, the beam limiting hole model, and the exit window model, respectively comprises:

simulating a secondary particle generated by the deflected particle in the range modulator model;

determining whether the secondary particle is able to pass through the range modulator model; and storing a state of the secondary particle in response to a passage of the secondary particle through the range modulator model.

20. A non-transitory computer-readable storage medium storing instructions that, when executed by at least one processor, cause the at least one processor to perform a method for simulating a particle transport, the method comprising:

obtaining a virtual particle source;

simulating a deflection of the virtual particle source under a magnetic field to obtain a deflected particle;

modeling one or more of a range modulator, a beam limiting hole, and an exit window based on physical properties of the range modulator, the beam limiting hole, and the exit window, respectively, to obtain one or more of a range modulator model, a beam limiting hole model, and an exit window model; and simulating physical processes of the deflected particle in the one or more of the range modulator model, the beam limiting hole model, and the exit window model, respectively.

* * * * *